US012799048B2

United States Patent
(12) United States Patent
Kinsho et al.

(10) Patent No.: US 12,799,048 B2
(45) Date of Patent: Nov. 17, 2026

(54) PROCESS FOR PREPARING BETA-FARNESENES AND 2-(3-ALKENYL)-1,3-BUTADIENE COMPOUND HAVING RELATED STRUCTURE, AND SYNTHETIC INTERMEDIATE COMPOUND THEREOF

(71) Applicant: Shin-Etsu Chemical Co., Ltd., Tokyo (JP)

(72) Inventors: Takeshi Kinsho, Joetsu (JP); Yusuke Nagae, Joetsu (JP); Akihiro Baba, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 137 days.

(21) Appl. No.: 19/019,796

(22) Filed: Jan. 14, 2025

(65) Prior Publication Data

US 2025/0270152 A1 Aug. 28, 2025

(30) Foreign Application Priority Data

Jan. 16, 2024 (JP) ................................ 2024-004372

(51) Int. Cl.
*C07C 4/00* (2006.01)

(52) U.S. Cl.
CPC .................................... *C07C 4/00* (2013.01)

(58) Field of Classification Search
CPC ....... C07C 4/00; C07C 2531/02; C07C 1/322; C07C 21/215; C07C 22/04; C07C 315/00; C07C 317/14; C07C 2531/12; C07C 2531/14; C07C 2531/24; C07C 1/30; C07C 17/361
See application file for complete search history.

(56) References Cited

U.S. PATENT DOCUMENTS 3,848,000 A 11/1974 Menet et al.
2006/0052643 A1 3/2006 Prakash et al.

OTHER PUBLICATIONS

Alpoim, et al., "Ring opening reactions of vinyl cyclopropanes with para toluene sulphonyl iodide", Tetrahedron Letters, 29(33):4173-4176 (1988).
Philippe, et al., "Two new convenient syntheses of 14C-squalene from turbinaric acid", Journal of Labelled Compounds and Radiopharmaceuticals, 61:878-884 (2018).
Extended European Search Report corresponding to European Patent Application No. 25150407.2 (7 pages) (dated Jun. 17, 2025).
Corey, et al., "Simple synthesis of (+/−)-beta-trans-bergamotene", Tetrahedron Letters, 26(30):3535-3538 (1985).
Anet, E. F. L. J. , "Synthesis of (E,Z)-α-,(Z,Z)-α-, and (Z)-β-farnesene", Australian Journal of Chemistry, 23 (10):2101-2108 (1970).
Baeckstrom , et al., "A Synthesis of Trans-β-Farnesene from Myrcene which Includes a Modified Work up Method for DIBAH Reductions of Esters to Aldehydes", Synthetic Communications, 20(3):423-429 (1990).
Brieger , et al., "The Synthesis of trans, trans-α-Farnesene", The Journal of Organic Chemistry, 34(12):3789-3791 (1969).
Kang, et al., "A Convenient Synthesis of (E)-β-Farnesene", Bulletin of the Korean Chemical Society, 8(4):351-353 (1987).
Kang , et al., "A Practical Synthesis of (E)-β-Farnesene, the Alarm Pheromone of Aphids", Bulletin of the Korean Chemical Society, 7(2):157-158 (1986).
Kawashima , et al., "Highly Regio- and Stereoselective Ring-Opening Reaction of γ-Alkenyl-γ-butyrolactones with Allylsilanes in the Presence of Trimethyloxonium Salt Leading to Methyl 4,8-Alkadienoates", Bulletin of the Chemical Society of Japan, 61(11):4051-4055 (1988).
Knight , et al., "(Z,E)-α-farnesene: Major component of secretion from metathoracic scent gland of cotton seed bug, Oxycarenus hyalinipennis (Costa) (Heteroptera; Lygaeidae)", Journal of Chemical Ecology, 10:641-649 (1984).
Mandai , et al., "Highly Stereoselective Total Syntheses of β-Farnesene, β-Sinensal, and Dendrolasin Employing 2-(Hydroxymethyl)-4-(phenylthio)-1-butene as a Building Block", The Journal of Organic Chemistry, 48(26):5183-5185 (1983).
Mimura , et al., "Synthetic Utility of Allylic Thiolcarbamates. Stereoselective Synthesis of Simple Natural Products Including Optically Active Manicone and β-Sinensal", Chemistry Letters, 8(11):1361-1364 (1979).
Morgan , et al., "Synthesis of (Z,E)- and (Z,Z)-α-farnesenes and -homofarnesenes", Journal of the Chemical Society, Perkin Transactions 1, pp. 399-404 (1985).

(Continued)

*Primary Examiner* — Ali Z Fadhel
(74) *Attorney, Agent, or Firm* — Myers Bigel, P.A.

(57) ABSTRACT

The present invention provides a process for preparing a 2-(3-alkenyl)-1,3-butadiene compound of the following general formula (A), wherein $R^1$ and $R^2$ represent, independently of each other, a hydrogen atom or a linear, branched, or cyclic hydrocarbon group having 1 to 20 carbon atoms and optionally having an unsaturated bond(s), the process comprising the step of subjecting a secondary allylsulfone compound of the following general formula (G), wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to a reductive removal of an arenesulfonyl group, W, at an allyl position, and then subjecting the secondary allylsulfone compound (G) to an elimination reaction of a hydrogen halide, HZ, in this order or in reverse order, to form the 2-(3-alkenyl)-1,3-butadiene compound (A).

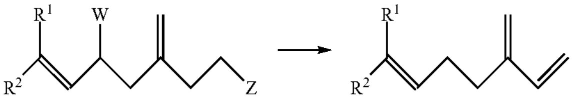

(G) (A)

6 Claims, No Drawings

(56) References Cited

OTHER PUBLICATIONS

Poppe , et al., "A Convenient Synthesis of (E)-β-Farnesene", Synthetic Communications, 17(2):173-179 (1987).
Ramaiah , et al., "A Short Synthesis of (3Z,6E)-α-Farnesene", The Journal of Organic Chemistry, 60:6211-6213 (1995).
Suckling , et al., "Trail Pheromone Disruption of Red Imported Fire Ant", Journal of Chemical Ecology, 36 (7):744-750 (2010).
Tanaka, et al., "A General Method for the Synthesis of 1,3-dienes. Simple Synthesis of β- and trans-α-Farnesene from Farnesol", Journal of the American Chemical Society, 97(11):3252-3254 (1975).
Vander Meer , et al., "Hydrocarbon components of the trail pheromone of the red imported fire ant, Solenopsis invicta", Tetrahedron Letters, 22(18):1651-1654 (1981).
Veselovskii , et al., "Regiospecific ene reaction of benzenesulfonyl chloride with linear isoprenoids", Organic Chemistry, 36:2583-2586 (1987).

PROCESS FOR PREPARING BETA-FARNESENES AND 2-(3-ALKENYL)-1,3-BUTADIENE COMPOUND HAVING RELATED STRUCTURE, AND SYNTHETIC INTERMEDIATE COMPOUND THEREOF

TECHNICAL FIELD

The present invention relates to a process for preparing β-farnesenes, which are sesquiterpenes useful as fragrances and flavors, or as biologically active substances against insects and the like, and 2-(3-alkenyl)-1,3-butadiene compounds having related structures. The present invention also relates to useful synthetic intermediate compounds thereof.

BACKGROUND ART

Farnesenes, which are known for a long time terpene compounds, have alpha and beta forms, differing by the positions of double bonds. α-Farnesene has four geometric isomers with trisubstituted double bonds at positions 3 and 6, and β-farnesene has two geometric isomers with a trisubstituted double bond at position 6:

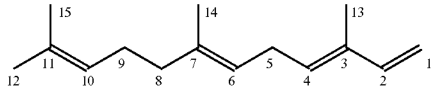

(3E,6E)-α-farnesene

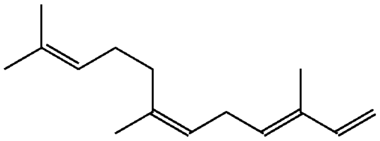

(3E,6Z)-α-farnesene

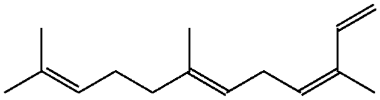

(3Z,6E)-α-farnesene

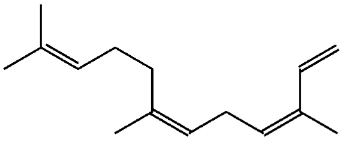

(3Z,6Z)-α-farnesene

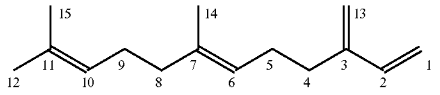

(E)-β-farnesene

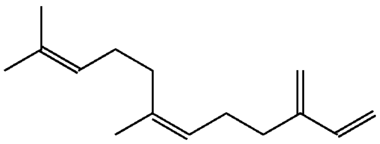

(Z)-β-farnesene wherein the numerals represent carbon positions.

Among farnesenes, α-farnesene has been identified in many plants, such as apples, pears, *Chrysanthemum, Perilla*, and *Achillea*. (3E,6E)-α-Farnesene is abundant in the skin of apple fruit, a natural source of this compound, and gives off a green apple odor. (3Z,6E)-α-Farnesene is found in essential oils of plants, such as *Perilla* and *Gardenia*. α-Farnesene also is found in extracts of many insects including several ants and the cotton seed bug, *Oxycarenus hyalinipennis*, and diverse biological activity has been reported. Examples include a trail pheromone of the hymenopteran, red imported fire ant, *Solenopsis invicta*; an alarm pheromone of the isopteran, termite; aggregation pheromones of the dipterans, Caribbean fruit fly and Mediterranean fruit fly; and an attractant of the lepidopteran, codling moth. β-Farnesene is a component of essential oils of various plants, and is known to have alarm pheromone activity against the hemipteran, aphid. These naturally-occurring and synthetic farnesenes also are used as fragrances and flavors as applications of biological activity of the human sense of smell.

β-Farnesenes are characterized by a 2-(3-alkenyl)-1,3-butadiene structure shown below:

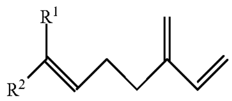

2-(3-alkenyl)-1,3-butadiene wherein $R^1$ and $R^2$ represent, independently of each other, a hydrogen atom or a linear, branched, or cyclic hydrocarbon group having 1 to 20 carbon atoms and optionally having an unsaturated bond(s).

β-Farnesenes correspond to when one of $R^1$ and $R^2$ is a methyl group, and the other is a 4-methyl-3-pentenyl group. Other important related compounds having this characteristic structure also are known. Known examples of related compounds include the corresponding monoterpenes and β-myrcene. Myrcenes, such as β-myrcene and its isomer, α-myrcene, which will be described in detail below, are found in plants such as *Laurus*, vervain (*Verbena*), caraway (*Carum*), fennel (*Foeniculum*), *Artemisia, Anethum, Angelica, Myrcia, Pinus, Amomum, Mentha, Salvia, Humulus*, and *Cannabis*. Myrcene is a pheromone of the coleopteran, *Scolytidae*, and acts as an attractant.

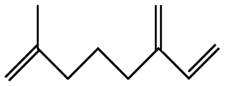

α-myrcene

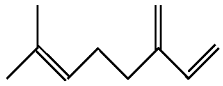

β-myrcene

PRIOR ART

Non-Patent Literatures

[Non-Patent Literature 1]R. K. Vander Meer et al., Tetrahedron Lett., 1981, 22, 1651.

[Non-Patent Literature 2]T. Nakai et al., Chem. Lett., 1979, 1361.

[Non-Patent Literature 3]J. Otera et al., J. Org. Chem., 1983, 48, 5183.

[Non-Patent Literature 4]S. -K. Kang et al., Bull. Korean Chem. Soc., 1986, 7, 157.

[Non-Patent Literature 5]C. Stántay et al., Synth. Commun., 1987, 17, 173.

[Non-Patent Literature 6]S. -K. Kang et al., Bull. Korean Chem. Soc., 1987, 351.

[Non-Patent Literature 7]V. V. Veselovskii et al., Izv. Akad. Natuk SSSR, Ser. Khim., 1987, 2787.

[Non-Patent Literature 8]M. Kawashima et al., Bull. Chem. Soc. Japan, 1988, 61, 4051.

[Non-Patent Literature 9]P. Baeckström et al., Synth. Commun., 1990, 20, 423.

OBJECT OF THE INVENTION

The economic synthesis and preparation of such farnesenes and their related derivatives are necessary for basic and applied research, and/or practical use. Isomers that occur naturally in large amounts may be sold inexpensively, while unnatural isomers that do not occur in nature are supplied by synthesis. Various other isomers may be obtained by the isomerization of natural products, but such isomers are typically complex isomeric mixtures, making it quite difficult to isolate and improve the purity of a specific isomer. To meet the needs of, for example, basic research such as comparative studies of isomer activity and correlation studies of the activity of derivatives with partially modified structures, it is desirable to selectively synthesize isomers by position and geometrical isomerism of the double bonds, and to have a higher degree of freedom for derivative synthesis by substituting substituent groups. Large amounts need to be synthesized for applications and practical use of pheromone activity for pest forecasting and pest control of organisms, such as insects, and for fragrances and flavors using the fragrance activity of humans, and it is desirable for the synthesis efficiency to be high enough to scale up for industrial purposes. Some applications and practical uses may not always require a pure isomer, and it may be economically advantageous to use a mixture of active isomers. For such purposes, there has been a high demand for a process applicable to both basic and applied research for efficiently preparing farnesenes and their related derivatives.

Various processes for synthesizing β-farnesenes are known. However, many known processes yield complex mixtures, from which pure compounds are isolated and purified with great difficulty. Non-Patent Literature 1, for example, describes dehydrating nerolidols to obtain α- and β-farnesene isomeric mixtures, of which isomers were separated by Florisil chromatography. Non-Patent Literature 2 reports synthesis in eight steps from β-myrcene, Non-Patent Literature 3 reports synthesis in twelve steps from 2-(hydroxymethyl)-4-(phenylthio)-1-butene, and Non-Patent Literature 4 reports synthesis in six steps from linalool. Non-Patent Literature 5 reports efficient synthesis in three steps from 3-methyl-3-butenol, Non-Patent Literature 6 reports efficient synthesis in two steps from farnesol, Non-Patent Literature 7 reports efficient synthesis in three steps from the starting material, unsaturated lactone, and Non-Patent Literature 8 reports efficient synthesis in three steps from β-myrcene. However, the stability of intermediates is a major problem for industrial-scale preparation when such synthesis is carried out from a raw material having a conjugated diene structure that is unstable thermally and in the presence of acids, or by forming a conjugated diene structure as an intermediate of the initial synthesis, such as in Non-Patent Literatures 2, 7, 8, and 9. Synthesis from natural products as starting materials, such as the synthesis of Non-Patent Literatures 2, 4, 6, 7, 8, and 9, is limited to specific raw materials that are available, and various derivatives with modified structures are not easy to synthesize. Industrial applications are unfeasible when a highly toxic reagent is used, such as selenium oxide of Non-Patent Literature 2, mercury(II) acetate of Non-Patent Literature 3, the chromium oxidation reagent, pyridinium chlorochromate (PCC), of Non-Patent Literature 4, and hexamethylphosphoric triamide (HMPA) of Non-Patent Literatures 3 and 5, or when special manufacturing equipment is required for a photoreaction, such as in Non-Patent Literature 9, or when low-temperature reactions are used, such as in Non-Patent Literatures 2, 3, 5, 6, and 9.

Thus, the known processes for synthesizing β-farnesene have many problems, and there has been a great need for an efficient process for preparing β-farnesenes and their related derivatives to overcome these problems.

SUMMARY OF THE INVENTION

As a result of intensive research in view of the aforesaid circumstances, it was found that a secondary allylsulfone compound, that will be explained below, could be designed as a reasonable synthetic intermediate and used as a synthetic route to selectively and efficiently prepare β-farnesenes and related 2-(3-alkenyl)-1,3-butadiene compounds, thus completing the present invention. The preparation process according to the present invention may be industrially advantageous as well.

According to an aspect of the present invention, there is provided a process for preparing a 2-(3-alkenyl)-1,3-butadiene compound of the following general formula (A):

(A)

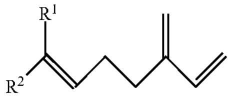

wherein $R^1$ and $R^2$ represent, independently of each other, a hydrogen atom or a linear, branched, or cyclic hydrocarbon group having 1 to 20 carbon atoms and optionally having an unsaturated bond, the process comprising the step of:

subjecting a secondary allylsulfone compound of the following general formula (G):

(G)

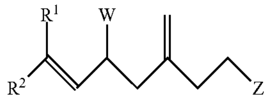

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to a reductive removal of an arenesulfonyl group, W, at an allyl position, and then subjecting the secondary allylsulfone compound (G) to an elimination reaction of a hydrogen halide, HZ, in this order or in reverse order, to form the 2-(3-alkenyl)-1,3-butadiene compound (A).

According to another aspect of the present invention, there is provided a process for preparing a 2-(3-alkenyl)-1,3-butadiene compound of the following general formula (A):

(A)

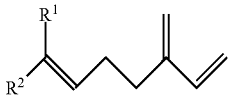

wherein $R^1$ and $R^2$ represent, independently of each other, a hydrogen atom or a linear, branched, or cyclic hydrocarbon group having 1 to 20 carbon atoms and optionally having an unsaturated bond(s), the process comprising the steps of:

subjecting a secondary allylsulfone compound of the following general formula (G):

(G)

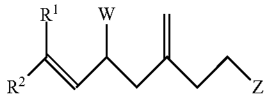

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to a reductive removal of an arenesulfonyl group, W, at an allyl position to form a halide compound of the following general formula (D):

(D)

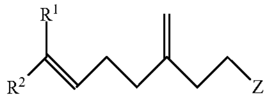

wherein $R^1$ and $R^2$ represent, independently of each other, a hydrogen atom or a linear, branched, or cyclic hydrocarbon group having 1 to 20 carbon atoms and optionally having an unsaturated bond(s), and Z represents a halogen atom; and subjecting the halide compound (D) thus obtained to an elimination reaction of a hydrogen halide, HZ, to form the 2-(3-alkenyl)-1,3-butadiene compound (A).

According to another aspect of the present invention, there is provided a process for preparing a 2-(3-alkenyl)-1,3-butadiene compound of the following general formula (A):

(A)

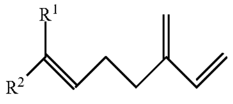

wherein $R^1$ and $R^2$ represent, independently of each other, a hydrogen atom or a linear, branched, or cyclic hydrocarbon group having 1 to 20 carbon atoms and optionally having an unsaturated bond(s), the process comprising the steps of:

subjecting a secondary allylsulfone compound of the following general formula (G):

(G)

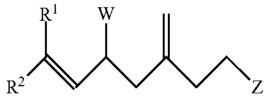

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to an elimination reaction of a hydrogen halide, HZ, to form a secondary allylsulfone compound of the following general formula (E):

(E)

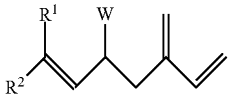

wherein $R^1$ and $R^2$ represent, independently of each other, a hydrogen atom or a linear, branched, or cyclic hydrocarbon group having 1 to 20 carbon atoms and optionally having an unsaturated bond(s), and W represents an arenesulfonyl group; and subjecting the secondary allylsulfone compound (E) thus obtained to a reductive removal of the arenesulfonyl group, W, at an allyl position to form the 2-(3-alkenyl)-1,3-butadiene compound (A).

According to another aspect of the present invention, there is provided a secondary allylsulfone compound of the following general formula (G):

(G)

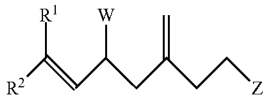

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom.

According to another aspect of the present invention, there is provided a halide compound of the following general formula (D'):

(D')

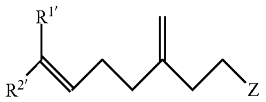

wherein one of $R^{1'}$ and $R^{2'}$ represents a methyl group, the other of $R^{1'}$ and $R^{2'}$ represents a 4-methyl-3-pentenyl group or a methyl group, and Z represents a halogen atom.

According to the present invention, β-farnesenes and 2-(3-alkenyl)-1,3-butadiene compounds having related structures may be selectively and efficiently prepared.

DETAILED DESCRIPTION OF THE INVENTION

Embodiments of the present invention will be explained below in detail. It should be understood that the present invention is not limited to or by the following embodiments.

Structures of intermediates, reagents, and target compounds represented by chemical formulae in the present specification may sometimes comprise stereoisomers, such as enantiomers or diastereomers. Unless otherwise stated, the chemical formulae shall be interpreted to represent all of these isomers. The isomers may be used alone or in combination at any ratio. A 50:50 mixture of two enantiomers is a racemic mixture, and a mixture containing two enantiomers at a non-equivalent ratio is a scalemic mixture. Either a racemic mixture or a scalemic mixture may be used.

The present inventors have investigated, according to a synthetic plan explained below, a process for preparing β-farnesenes and 2-(3-alkenyl)-1,3-butadiene compounds having related structures:

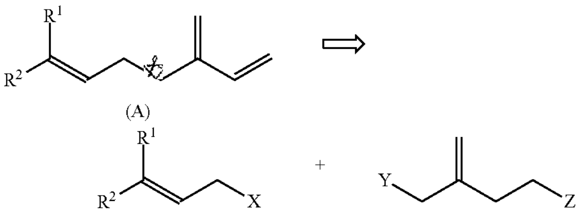

(A) (B) + (C)

wherein the white arrow represents a transform in retrosynthetic analysis, the scissors mark represents disconnection of a bond in the retrosynthetic analysis, $R^1$ and $R^2$ represent, independently of each other, a hydrogen atom or a linear, branched, or cyclic hydrocarbon group having 1 to 20 carbon atoms and optionally having an unsaturated bond(s), and X, Y, and Z represent, independently of each other, a halogen atom.

In the aforesaid synthesis plan, the case where one of $R^1$ and $R^2$ represents a methyl group and the other of $R^1$ and $R^2$ represents a 4-methyl-3-pentenyl group corresponds to β-farnesene. More specifically, the case where $R^1$ represents a methyl group and $R^2$ represents a 4-methyl-3-pentenyl group corresponds to (E)-β-farnesene, and the case where $R^1$ represents a 4-methyl-3-pentenyl group and $R^2$ represents a methyl group corresponds to (Z)-β-farnesene.

First, it was thought that the disconnection of the bond illustrated by the aforesaid scissors in the synthesis of the targets, β-farnesene and the 2-(3-alkenyl)-1,3-butadiene compound (A), which have 2-substituted butadiene at the end, would be reasonable due to the availability of C5 reagents (having 5 carbon atoms) based on the isoprene rule of terpenes and the ease of synthesizing derivatives. The bond-forming reactive sites of the carbon-carbon bond-forming reaction between the intermediate building blocks (B) and (C) each are the allyl position, and so difficulties were expected for homocoupling of the nucleophile side and the electrophile side in typical Grignard coupling (a carbon-carbon bond-forming reaction between a Grignard reagent and a halide compound) and the like. Therefore, the application of a process of a carbon-carbon bond-forming reaction by allylation of the anion at the α-position of the sulfone and a desulfonation reaction in a subsequent step was thought to be as follows:

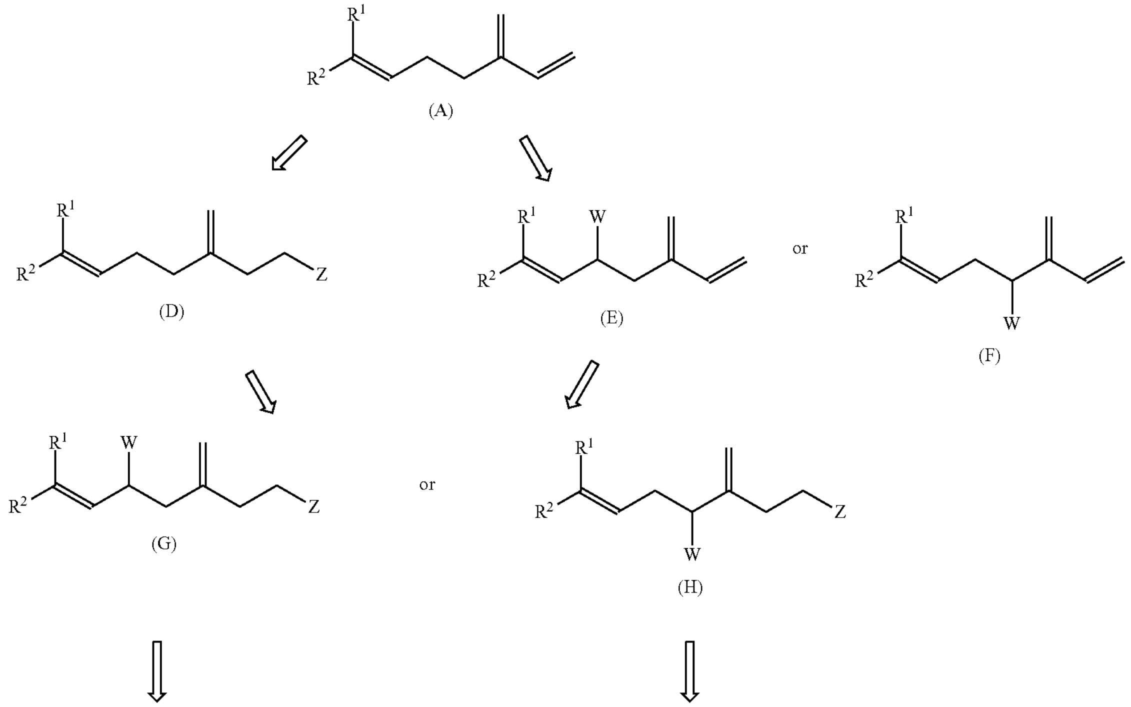

(A) (D) (E) or (F) (G) or (H)

-continued

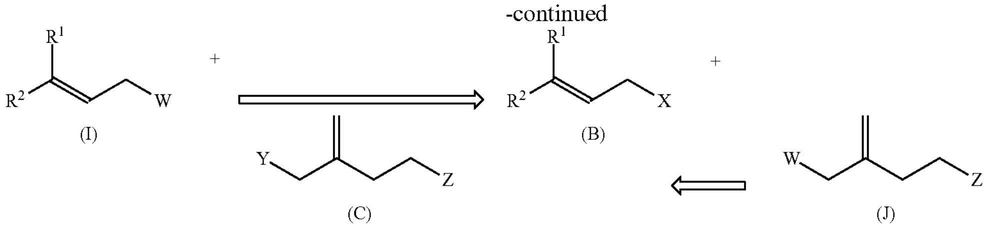

(I) (C) (B) (J)

wherein the white arrows represent transformation in retrosynthetic analysis, $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and X, Y, and Z represent, independently of each other, a halogen atom.

Secondary allylsulfone compounds (G) and (H) having different positions of the sulfone, i.e., arenesulfonyl group, W, were designed as key synthetic intermediates. It was thought that the secondary allylsulfone compound (G) may be obtained by allylation with the dihalide compound (C) of an α-anion prepared from the primary allylsulfone compound (I), and that the secondary allylsulfone compound (H) may be obtained by allylation with the halide compound (B) of an α-anion prepared from the primary allylsulfone compound (J). The primary allylsulfone compounds (I) and (J) may be synthesized from the halide compound (B) and the dihalide compound (C), respectively. Specifically, one of the compounds (B) and (C) is converted into a sulfone compound, and an α-anion prepared from the sulfone compound thus obtained is subjected to allylation with the other of the compounds (B) and (C) to form the key intermediate, secondary allylsulfone compound (G) or (H).

The secondary allylsulfone compound (G) or (H) is subjected to reductive removal of an arenesulfonyl group, W, at the allyl position of the secondary allylsulfone compound (G) or (H) (i.e., desulfonation) (or a reductive cleavage of an arenesulfonyl group, W, at allyl position from the secondary allylsulfone compound (G)) to form the halide compound (D), and then the halide compound (D) is subjected to an elimination reaction of the hydrogen halide, HZ, of the halide compound (D) to form the 2-(3-alkenyl)-1,3-butadiene compound (A). Alternatively, by interchanging the order of converting the functional groups, a hydrogen halide, HZ, is eliminated from the secondary allylsulfone compound (G) or (H) to form the secondary allylsulfone compound (E) or (F), and then the secondary allylsulfone compound (E) or (F) is subjected to a reductive removal of an arenesulfonyl group, W, (i.e., desulfonation) to form the 2-(3-alkenyl)-1,3-butadiene compound (A).

Many of the intermediates, such as sulfone intermediates having exo-double bonds, of the aforesaid synthesis plan are novel compounds, and while not reported in the Synthetic Examples and the Reaction Examples, were subjected to intensive research based on the aforesaid synthesis plan.

As a result of intensive research based on the aforesaid investigation, the present inventors successfully realized the desired reaction, and efficiently synthesized β-farnesenes and related 2-(3-alkenyl)-1,3-butadiene compounds. Embodiments of the present invention will be described by each step in detail below.

Target compounds of the present invention, 2-(3-alkenyl)-1,3-butadiene compounds Target compounds of the present invention, β-farnesenes and 2-(3-alkenyl)-1,3-butadiene compounds having related structures, will be explained in detail below. A 2-(3-alkenyl)-1,3-butadiene compound is represented by the following general formula (A):

(A)

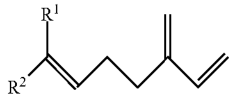

wherein $R^1$ and $R^2$ represent, independently of each other, a hydrogen atom or a linear, branched, or cyclic hydrocarbon group having 1 to 20 carbon atoms and optionally having an unsaturated bond(s).

The hydrocarbon groups $R^1$ and $R^2$ are a hydrogen atom or a hydrocarbon group having 1 to 20, preferably 1 to 17, and more preferably 1 to 12 carbon atoms. Specific examples of the hydrocarbon groups $R^1$ and $R^2$ include linear alkyl groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group; branched alkyl groups such as an isopropyl group, an isobutyl group, a sec-butyl group, a tert-butyl group, an isopentyl group, and an alkyl group wherein one to six hydrogen atoms of the aforesaid linear alkyl group are substituted with a methyl group or an ethyl group; and a cyclic alkyl group with a cyclic structure such as cyclopropane, cyclobutane, cyclopentane, cyclohexane, and benzene. Examples of the unsaturated bond of the hydrocarbon group R include a double bond and a triple bond. The unsaturated bond of the hydrocarbon group R is preferably a double bond. One to five unsaturated bonds are preferred. One of $R^1$ and $R^2$ represents, for example, a methyl group; and the other of $R^1$ and $R^2$ represents a 4-methyl-3-pentenyl group or a methyl group. Or, one of $R^1$ and $R^2$ represents a phenyl group; and the other of $R^1$ and $R^2$ represents a hydrogen atom.

Synthesis of Starting Materials, Allylsulfone Compounds (I) and (J)

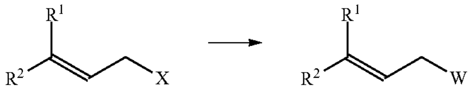

(B) (I)

-continued

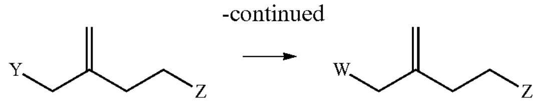

(C) (J)

wherein $R^1$ and $R^2$ represent, independently of each other, a hydrogen atom or a linear, branched, or cyclic hydrocarbon group having 1 to 20 carbon atoms and optionally having an unsaturated bond(s), X, Y, and Z represent, independently of each other, a halogen atom, and W represents an arenesulfonyl group.

Although the process for synthesizing the starting materials of the present invention, allylsulfone compounds (I) and (J), is not particularly limited, the allylsulfone compounds (I) and (J) are obtained, for example, by mixing arenesulfinate salt with the allyl halide compound (B) and the dihalide compound (C), latter of which has exo-methylene, and heating in a solvent to substitute the halogen atom X or Y at the allyl position with an arenesulfonyl group, W. X of allyl halide compound (B) and Y and Z of the dihalide compound (C) are, independently of each other, a halogen atom, preferably a chlorine atom, a bromine atom, and an iodine atom, and even more preferably a chlorine atom or a bromine atom. The allyl halide compound (B) and the dihalide compound (C) may be commercially available or may be synthesized by a known process. In the allyl halide compound (B), $R^1$ and $R^2$ may be optionally determined, independently of each other, from a hydrogen atom or a linear, branched, or cyclic hydrocarbon group having 1 to 20 carbon atoms and optionally having an unsaturated bond(s) to correspond to the target compound. X is preferably a chlorine atom, a bromine atom, or an iodine atom. Specific examples of the dihalide compound (C) include 4-chloro-2-chloromethyl-1-butene, 2-bromomethyl-4-chloro-1-butene, 4-bromo-2-chloromethyl-1-butene, and 4-bromo-2-bromomethyl-1-butene. Instead of the halogen atoms X, Y, and Z, a pseudo-halogen group that functions as a leaving group in the aforesaid substitution reactions, alkylation (a carbon-carbon bond-forming reaction) of α-anions and elimination of HZ for olefin formation, that will be explained below, may be used, such as phosphoryloxy groups such as a dimethylphosphoryloxy group, a diethylphosphoryloxy group, and a diphenylphosphoryloxy group; and sulfonyloxy groups such as a methanesulfonyloxy group, a trifluoromethanesulfonyloxy group, a nonafluorobutanesulfonyloxy group, a benzenesulfonyloxy group, and a p-toluenesulfonyloxy group, which are generally referred to as halogen atoms in the present specification hereinafter. W in the allylsulfone compounds (I) and (J) is an arenesulfonyl group. Because sodium benzenesulphinate and sodium p-toluenesulphinate are commercially available industrially as corresponding metal arenesulfinates used as reagents, an arenesulfonyl group, W, is preferably a benzenesulfonyl group and a p-toluenesulfonyl group. The regioselectivity of the conversion from the dihalide compound (C) to the allylsulfone compound (J) is high, and the halogen atom Y at the allyl position reacts preferentially compared to the halogen atom Z at the position of a homoallyl to form the allylsulfone compound (J) with high yield. Strictly speaking, W in $WM^1$ is a compound of an arylsulfenyl group Ar—S(═O)—O— in which an oxygen atom O is bonded to the metal atom $M^1$, and W in the sulfone compounds (I) and (J) is a compound of an arylsulfonyl group Ar—S(═O)$_2$— in which a sulfur atom S is bonded to a carbon atom C.

Allylation step of the secondary allylsulfone compound (G) from the allylsulfone compound (I) with the dihalide compound (C):

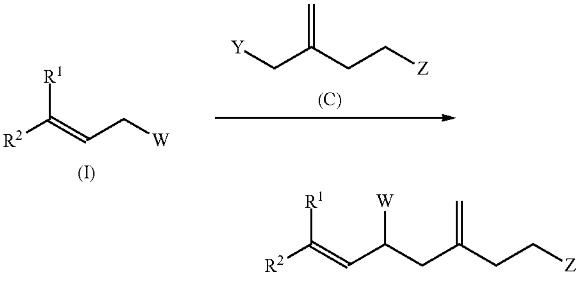

(C) (I) (G)

wherein $R^1$, $R^2$, W, Y, and Z are as defined above, and

Allylation step of secondary allylsulfone compound (H) from allylsulfone compound (J) with allyl halide compound (B):

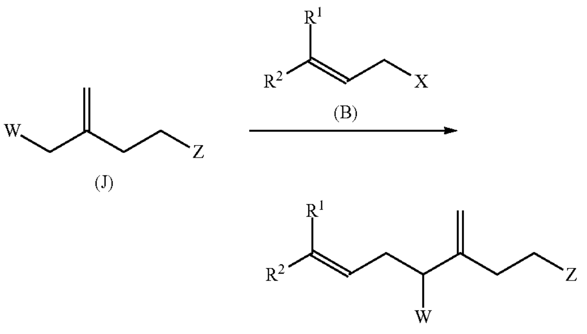

(B) (J) (H)

wherein $R^1$, $R^2$, W, X, and Z are as defined above.

Each of these allylation steps is an allylation reaction of position a of the sulfone. The reaction is typically carried out by subjecting the sulfone compound (I) to α-anion formation with a base in a solvent, and by allylation of the resulting anion with the allyl electrophile, dihalide compound (C), or by subjecting the sulfone compound (J) to α-anion formation, and by allylation of the resulting anion with the allyl electrophile, allyl halide compound (B):

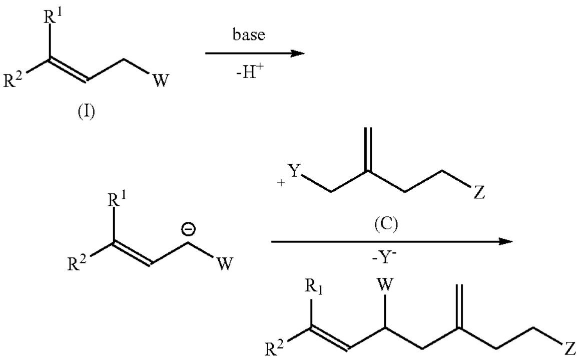

(I) (C) (G)

-continued

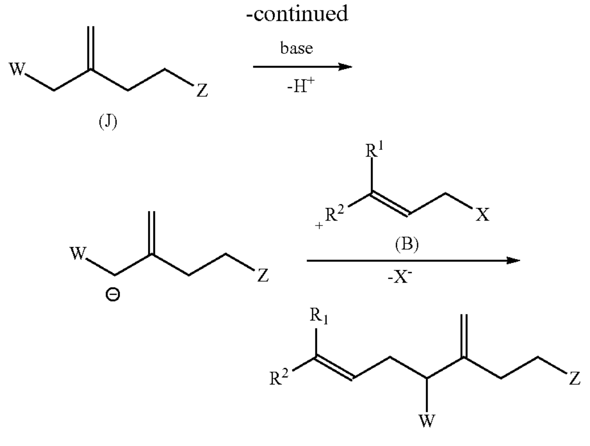

(J)
(B)
(H)

wherein "base" represents a base, and $R^1$, $R^2$, W, X, Y, and Z are as defined above.

Although the base used in the anion formation is not particularly limited as long as an anion can be formed at position a of the sulfone compound, examples of the base include inorganic bases such as sodium hydride, potassium hydride, calcium hydride, sodium amide, potassium amide, sodium hydroxide, and potassium hydroxide; organic bases such as triethylamine, tributylamine, diisopropylethylamine, 1,5-diazabicyclo[4.3.0]-5-nonene (DBN), 1,4-diazabicyclo [2.2.2]octane (DABCO), and 1,8-diazabicyclo[5.4.0]-7-undecene (DBU); alkoxides such as sodium methoxide, sodium ethoxide, lithium tert-butoxide, and potassium tert-butoxide; alkyllithiums such as methyllithium, ethyllithium, n-butyllithium, sec-butyllithium, and tert-butyllithium; Grignard reagents such as methylmagnesium halide (including chloride, bromide, and iodide; hereinafter the same shall apply), ethylmagnesium halide, and phenylmagnesium halide; alkyl metal compounds such as dimethylzinc, diethylzinc, trimethylaluminum, triethylaluminum, and methylaluminumdichloride; and metal amides such as lithium diethylamide, lithium diisopropylamide, lithium isopropylcyclohexylamide, lithium hexamethyldisilazide, sodium hexamethyldisilazide, and halomagnesium hexamethyldisilazide. Any base selected from these is used alone, or in any combination thereof. Halide salts such as lithium chloride may be added. The base is particularly preferably alkyllithiums, Grignard reagents, and metal amides.

As the electrophile used in the allylation, X of the allyl halide compound (B) and Y and Z of the dihalide compound (C) are, independently of each other, a halogen atom. The halogen atom is particularly desirably a chlorine atom, a bromine atom, and an iodine atom.

Examples of the solvent include ethers such as diethyl ether, dibutyl ether, diethyleneglycol diethyl ether, diethyleneglycol dimethyl ether, tetrahydrofuran, 4-methyltetrahydropyran, and 1,4-dioxane; hydrocarbons such as hexane, heptane, benzene, toluene, xylene, and cumene; chlorinated solvents such as methylene chloride, chloroform, and trichloroethylene; nitriles such as acetonitrile; ketones such as acetone and 2-butanone; esters such as ethyl acetate and butyl acetate; and aprotic polar solvents such as N,N-dimethylformamide, dimethyl sulfoxide, and hexamethylphosphoric triamide. Any solvent selected from these is used alone, or in any combination thereof.

A more appropriate reaction temperature may be selected according to the type of base used and reaction conditions. Typically, the reaction temperature is preferably −50° C. to the boiling point of the solvent, and more preferably −20° C. to a room temperature (5° C. to 35° C.; hereinafter the same shall apply).

Although the reaction time may be arbitrarily set, the conversion and/or the isomer ratio may be optimized by monitoring with gas chromatography (GC) or thin layer chromatography (TLC). The reaction time is typically and preferably 5 minutes to 240 hours.

When the secondary allylsulfone compounds (G) and (H) obtained in the aforesaid alkylation step and a halogen exchange step, that will be explained below, have sufficient purity and isomer ratios, the secondary allylsulfone compounds (G) and (H) may be incorporated in a subsequent step as a crude product. However, purification and isomer separation may be selected from any suitable purification method or isomer separation process used in usual organic synthesis such as distillation or various chromatography.

Next, the following two processes are possible as synthetic routes from the secondary allylsulfone compound (G) or (H) thus obtained to the 2-(3-alkenyl)-1,3-butadiene compound (A).

(I) A process via the halide compound (D), specifically, (I)-(1) reductive removal of an arenesulfonyl group, W, at an allyl position of the secondary allylsulfone compound (G) or (H) (i.e., desulfonation) to form a halide compound (D), and then (I)-(2) elimination reaction of a hydrogen halide, HZ, of the halide compound (D) to form the target compound, 2-(3-alkenyl)-1,3-butadiene compound (A):

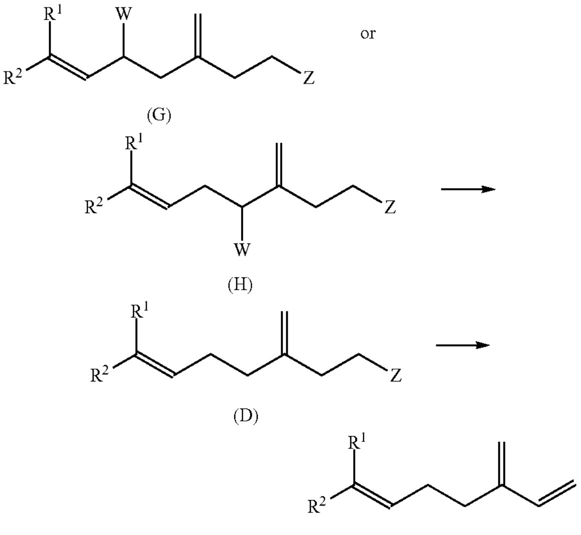

(G)
or
(H)
(D)
(A)

wherein $R^1$, $R^2$, W, and Z are as defined above.

(II) Process via the secondary allylsulfonediene compound (E) or (F), specifically, (II)-(1) elimination reaction of a hydrogen halide, HZ, of the secondary allylsulfone compound (G) or (H) to form a secondary allylsulfonediene compound (E) or (F), and then (II)-(2) reductive removal of an arenesulfonyl group, W, at an allyl position of the secondary allylsulfonediene compound (E) or (F) to form the target compound, 2-(3-alkenyl)-1,3-butadiene compound (A):

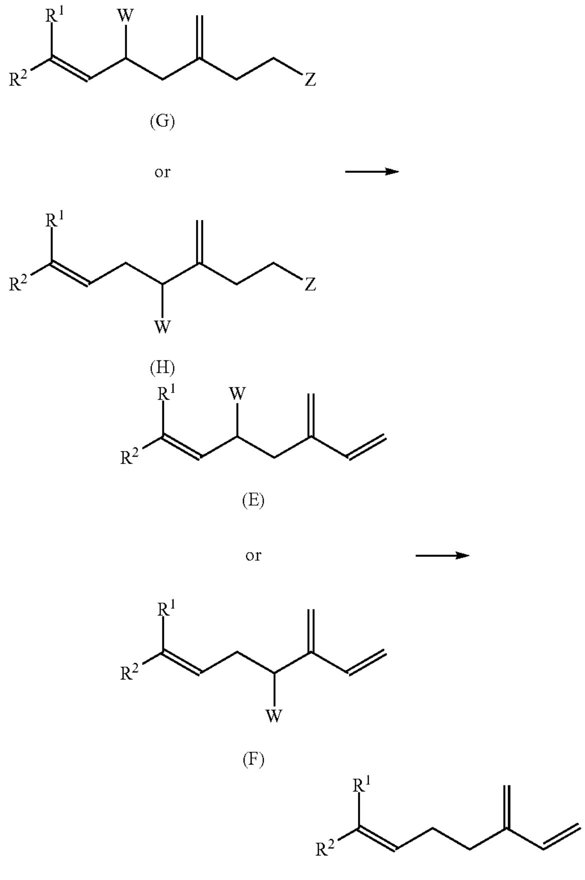

(G) or (H) (E) or (F) (A)

wherein $R^1$, $R^2$, W, and Z are as defined above.

The synthetic routes (I) and (II) are explained below in order, and their applications will be explained below.

(I)-(1) Reductive removal step of an arenesulfonyl group, W, at an allyl position of the secondary allylsulfone compound (G) or (H) to form the halide compound (D)

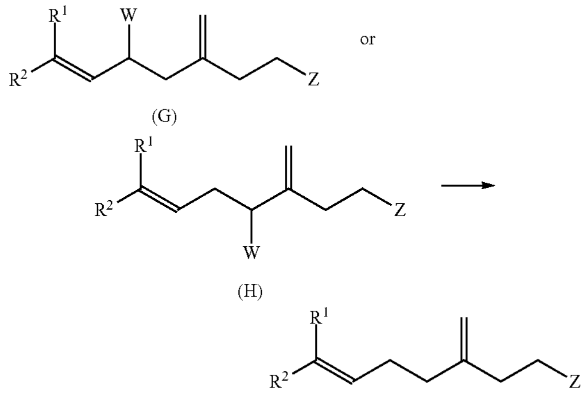

(G) or (H) (D)

wherein $R^1$, $R^2$, W, and Z are as defined above.

The reductive removal step is a step of substituting an arenesulfonyl group, W, with a hydrogen atom, H.

In the reductive removal (or a reductive cleavage) step, the reaction substrate, secondary allylsulfone compound (G)

or (H), may be a chloride compound (when Z═Cl), a bromide compound (when Z═Br), and an iodide compound (when Z═I). While the aforesaid compounds may be synthesized, for example, in "Halogen exchange step of intermediate" that will be explained below, a chloride compound is preferred as the substrate of the reductive removal (or reductive cleavage) step. By using said chloride compound, a preferred suppression of side reactions may be ensured.

Although the process used for the reductive removal (or reductive cleavage) may be a known process and is not particularly limited, examples include a direct electron reduction reaction with a metal or metal salt, a nucleophilic substitution reduction reaction with a hydride ($H^-$) nucleophilic reagent, and a radical substitution reduction reaction with a hydrogen radical ($H^-$) reagent.

Examples of reagents used in the direct electron reduction reaction with a metal or metal salt include alkali metals such as sodium and lithium; other metals such as magnesium, zinc, and tin; amalgams of various metals and combinations protic solvents such as lower amines such as ammonia, methylamine, ethylamine, and propylamine; lower alcohols such as methanol, ethanol, 1-propanol, 2-propanol, 1-butanol, and 2-butanol; carboxylic acids such as formic acid, acetic acid, and propionic acid; and metal salts such as samarium diiodide. Preferred specific examples of metal-protic solvents include lithium-ammonia, sodium-ammonia, sodium-lower amine, lithium-lower amine, magnesium-methanol, and zinc-acetic acid. It is preferred to use sodium-naphthalenide and Raney-nickel (Raney-Ni) in a solvent. Examples of amalgams include sodium-amalgam and aluminum-amalgam. Among these reagents, lithium-ammonia, sodium-ammonia, sodium-lower amine, lithium-lower amine, and magnesium-methanol are preferred. By using said lithium-ammonia, sodium-ammonia, sodium-lower amine, lithium-lower amine, and magnesium-methanol, a preferred industrial application may be ensured.

Examples of the hydride ($H^-$) nucleophilic reagent used in the nucleophilic substitution reduction reaction include borane compounds such as borane, alkylborane, dialkylborane, bis(3-methyl-2-butyl)borane; silane compounds such as dialkylsilane and trialkylsilane; alane compounds such as alkylaluminum dialkylaluminum (diisobutylaluminum hydride, etc.); metal hydrides such as sodium hydride, lithium hydride, potassium hydride, and calcium hydride; complex hydrides such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodium bis(2-methoxyethoxy)aluminum hydride, and lithium triethylborohydride; and alkoxy or alkyl derivatives thereof. Such complex hydrides also may be combined with formic acid as a hydride source. The transition metal catalyst may be incorporated in the nucleophilic reduction reaction. Examples of the transition metal catalyst include transition metal compounds such as nickel, rhodium, palladium, ruthenium, and iridium. Palladium compounds are particularly preferred. Examples of preferred palladium compounds include zerovalent palladium compounds and divalent palladium compounds. A phosphorus compound may be used as a ligand with these palladium compounds. Examples of the phosphorus compound used as the ligand include phosphines such as trimethylphosphine, tri-tert-butylphosphine, trioctylphosphine, tricyclohexylphosphine, tri(o-tolyl)phosphine, dimethylphenylphosphine, tri(2-furyl)phosphine, diphenyl-2-pyridylphosphine, tris(hydroxymethyl)phosphine, 1,2-bis(dimethylphosphino)ethane, bis(diphenylphosphino)methane, 1,2-bis(diphenylphosphino)ethane, 1,3-bis(diphenylphosphino)propane, 1,4-bis(diphenylphosphino)butane, 1,2-bis(dicyclohexylphosphino)ethane, and 2-dicyclohexylphosphino-2,6-dimethoxybiphenyl; and phosphite esters such as trimethylphosphite, triethylphosphite, and triphenylphosphite. Among these compounds, a combination of a complex hydride and a palladium compound is preferred. Combinations of lithium triethylborohydride with a transition metal catalyst; and lithium borohydride with formic acid and a transition metal catalyst are particularly preferred. By using said combinations of lithium triethylborohydride with a transition metal catalyst; and lithium borohydride with formic acid and a transition metal catalyst, particularly preferred stereospecificity (in this case, a substitution reaction of the $S_N2$ mechanism without allylic rearrangement) may be ensured. Although the aforesaid palladium compound is preferably zero-valent, a divalent palladium compound also is preferred due to the divalent metallic compound reducing to zero-valent under reduction conditions in the reaction system. Examples of the hydrogen radical ($H^-$) reagent used in the radical substitution reduction reaction include tributyltin hydride (TBTH). A radical initiator such as an azo compound such as 2,2'-azobisisobutyronitrile, dimethyl 2,2'-azobis(isobutyrate), and 1,1'-azobis(cyclohexanecarbonitrile); and an organic peroxide such as di-tert-butyl peroxide, tert-butyl hydroperoxide, and benzoyl peroxide may be used in combination in the radical reduction reaction.

In addition to the aforesaid protic solvents, examples of a solvent used in the reductive removal (or reductive cleavage) step include water; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, 1,4-dioxane, and 4-methyltetrahydropyran; alcohols such as methanol, ethanol, 1-propanol, 2-propanol, t-butyl alcohol, benzyl alcohol, methoxyethanol, and ethoxyethanol; ketones such as acetone and 2-butanone; nitriles such as acetonitrile and propionitrile; esters such as ethyl acetate and butyl acetate; and aprotic polar solvents such as N,N-dimethylformamide (DMF), 1,3-dimethyl-2-imidazolidinone (DMI), dimethyl sulfoxide (DMSO), and hexamethylphosphoric triamide (HMPA). The solvent is appropriately selected, depending on the type of reagent to be used, and may be used alone, or in any combination thereof. A reaction temperature of the reductive removal (or reductive cleavage) step varies, depending on the reagent and the solvent to be used, and is preferably −78° C. to 50° C., and more preferably −70 to 20° C. A reaction time may be arbitrarily set. In view of the yield, it is desirable to monitor progress of the reaction with gas chromatography (GC) and/or silica gel thin layer chromatography (TLC) to complete the reaction. The reaction time is typically and preferably 5 minutes to 240 hours.

Excessive reagents and extreme reaction conditions in the aforesaid reductive removal (or reductive cleavage) step should be avoided due to the risk of a side reaction in which not only an arenesulfonyl group, W, but also the halogen atom (halo group) Z is reductively removed and substituted with a hydrogen atom. It was found that the appropriate selection of the reagent types and reaction conditions gave good selectivity in which an arenesulfonyl group, W, was reductively removed while a halo group, Z, remained, and that Z is particularly preferably a chlorine atom.

A crude product of the halide compound (D) obtained from the aforesaid reductive removal (or reductive cleavage) step or the halogen exchange step, that will be explained below, may be used as such in a subsequent step when having a sufficient purity and isomer ratio. Alternatively, the crude product may be purified and separated into isomers in any purification method or isomer separation process used in usual organic synthesis such as distillation and/or various chromatography.

(I)-(2) Elimination Reaction Step of a Hydrogen Halide, HZ, from the Halide Compound (D) to the 2-(3-Alkenyl)-1,3-Butadiene Compound (a)

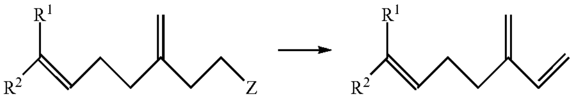

(D) (A)

wherein $R^1$, $R^2$, and Z are as defined above.

This elimination step typically may be carried out by eliminating HZ in a solvent or without a solvent, with heating or cooling, if necessary.

The reaction substrate of this elimination step, halide compound (D), may be a chloride compound (when Z═Cl), a bromide compound (when Z═Br), and an iodide compound (when Z═I). These compounds may be synthesized, for example, in "Halogen exchange step of intermediate" that will be explained below.

Examples of the base used in the elimination step include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; hydrides such as lithium hydride, sodium hydride, potassium hydride, and calcium hydride; hydroxide salts such as sodium hydroxide, lithium hydroxide, potassium hydroxide, and barium hydroxide; carbonates such as sodium carbonate, potassium carbonate, sodium bicarbonate, and potassium bicarbonate; organometallic reagents such as methyllithium, ethyllithium, n-butyllithium, and methylmagnesium chloride; metal amides such as lithium amide, sodium amide, lithium diisopropylamide, lithium hexamethyldisilazide, sodium hexamethyldisilazide, and lithium dicyclohexylamide; and organic bases such as triethylamine, diisopropylethylamine, tributylamine, diisopropylethylamine, N,N-dimethylaniline, N,N-diethylaniline, pyridine, 4-dimethylaminopyridine, quinoline, pyrrolidine, piperidine, collidine, lutidine, morpholine, piperazine, 1,5-diazabicyclo[4.3.0]-5-nonene (DBN), 1,4-diazabicyclo[2.2.2]octane (DABCO), and 1,8-diazabicyclo[5.4.0]-7-undecene (DBU). The base may be used alone, or in any combination thereof, and is selected, depending on the substrate type, reactivity, and/or selectivity. Preferred examples of the base include carbonates such as potassium carbonate; alkoxides such as potassium t-butoxide; and organic bases such as 1,5-diazabicyclo[4.3.0]-5-nonene (DBN), 1,4-diazabicyclo[2.2.2]octane (DABCO), and 1,8-diazabicyclo[5.4.0]-7-undecene (DBU). The amount of the base used is 0.01 to 100 mol, and preferably 0.1 to 10 mol, per mol of the substrate, halide compound (D). Examples of the solvent used in the elimination step include, in addition to the aforesaid protic solvents, water; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, 1,4-dioxane, and 4-methyltetrahydropyran; alcohols such as methanol, ethanol, 1-propanol, 2-propanol, t-butyl alcohol, benzyl alcohol, methoxyethanol, and ethoxyethanol; ketones such as acetone and 2-butanone; nitriles such as acetonitrile and propionitrile; esters such as ethyl acetate and butyl acetate; and aprotic polar solvents such as N,N-dimethylformamide (DMF), 1,3-dimethyl-2-imidazolidinone (DMI), dimethyl sulfoxide (DMSO), and hexamethylphosphoric triamide (HMPA). The solvent is appropriately selected, depending on the type of reagent to be used, and may be used alone, or in any combination thereof. A reaction temperature of the elimination step varies, depending on the reagent and/or the solvent used, and is preferably −78° C. to 200° C., and more preferably 0 to 100° C. A reaction time may be arbitrarily set. In view of the yield, it is desirable to monitor progress of the reaction with gas chromatography (GC) and/or silica gel thin layer chromatography (TLC) to complete the reaction. The reaction time is typically and preferably 5 minutes to 240 hours. The target compound, 2-(3-alkenyl)-1,3-butadiene compound (A), has a thermally unstable diene structure, and so reactions at high temperatures for long periods of time should be avoided. Mild conditions such that the reaction proceeds at low temperatures for short periods of time are preferred.

Next, the synthetic route (II) will be explained in detail below. The synthetic route (II) is the two steps of:

(II)-(1) Elimination reaction step of a hydrogen halide, HZ, from the secondary allylsulfone compound (G) or (H) to the secondary allylsulfonediene compound (E) or (F):

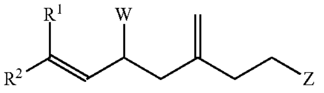

(G)

or

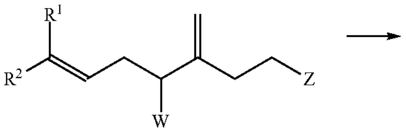

(H)

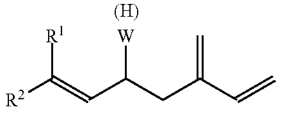

(E)

or

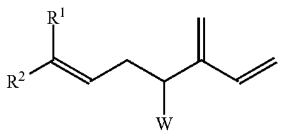

(F)

wherein $R^1$, $R^1$, W, and Z are as defined above, and (II)-(2) Reductive removal step of an arenesulfonyl group, W, at an allyl position from the secondary allylsulfonediene compound (E) or (F) to the 2-(3-alkenyl)-1,3-butadiene compound (A):

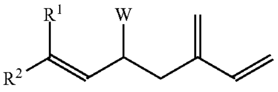

(E)

or

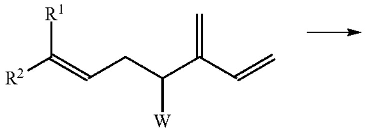

(F)

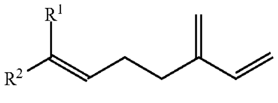

(A)

wherein $R^1$, $R^2$, W, and Z are as defined above.

The step (II)-(1) may be carried out by eliminating HZ, similarly to the aforementioned (I)-(2) "Elimination reaction step of a hydrogen halide, HZ, from the halide compound (D) to the 2-(3-alkenyl)-1,3-butadiene compound (A)". The step (II)-(2) may be carried out by reductively removing an arenesulfonyl group, W, at an allyl position, similarly to (I)-(1) "Reductive removal step of an arenesulfonyl group, W, at an allyl position from the secondary allylsulfone compound (G) or (H) to the halide compound (D)".

Among the synthetic routes mentioned above, it was found that, as an reductive removal (or a reductive cleverage) (i.e., desulfonylation) substrate of the secondary arenesulfone at the allyl position, the secondary allylsulfone compound (G) having arenesulfone positioned at an allyl position of the endo-olefin (the trisubstituted double bond) is more particularly suited to the synthesis of β-farnesene and its related derivatives of the present invention than the secondary allylsulfone compound (H) or (F) having the arenesulfone positioned at the allyl position of the exo-olefin (the disubstituted double bond), in view of stereospecificity of the reaction and the lack of a thermally unstable conjugated diene structure. Details will be elaborated in the Examples below.

(G)

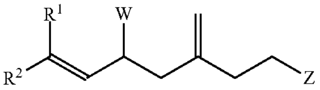

(H)

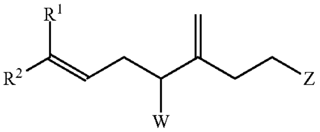

(F)

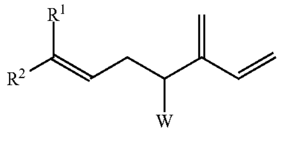

wherein $R^1$, $R^2$, W, and Z are as defined above.

Halogen Exchange Step of Intermediate

Among the intermediates of this preparation process, the secondary allylsulfone compound (G), the secondary allylsulfone compound (H), and the halide compound (D) have the halogen atom (halo group) Z and may be three types of compounds, specifically, a chloride compound, a bromide compound, and an iodide compound depending on the type of the halogen atom Z. One type of halide compound may be used as a starting material to synthesize, with a halogen conversion reaction, another type of halide compound to be used in the step. To improve the reactivity, it is preferred to convert to a halide compound having high reactivity such as, for example, converting from a chloride compound to a bromide compound, from a chloride compound to an iodide compound, and from a bromide compound to an iodide compound. The conversion may be selected based on the yield, the reactivity, and the stability of the intermediate. The halogen exchange reaction may be a known process such as heating a halide compound as a starting material such as, for example, a chloride compound and/or a bromide compound in a solvent with a halogen source such as a halide salt having a halide ion Z-such as, for example, $Br^-$ and/or $I^-$ of another halogen atom present in the target compound such as a bromide compound and/or an iodide compound. The halogen exchange reaction may be carried out in situ in the step. Although the halogen exchange reaction may be carried out with any of the secondary allylsulfone compound (G), the secondary allylsulfone compound (H), and the halide compound (D) as an intermediate, it is preferred to use an appropriate intermediate to avoid undesirable side reactions such as, for example, reduction of the halogen atom in the reductive removal step of an arenesulfonyl group, W. The appropriate intermediate is preferably the secondary allylsulfone compound (G) or the halide compound (D), and particularly preferably the halide compound (D).

Examples of advantages of the preparation process of the present invention above include the following:

(1) The stability of the synthetic intermediate, in the steps and in storage, is high because the unstable conjugated diene structure is constructed in the final stage of the synthesis or in one step previous.

(2) When the substituent groups $R^1$, $R^2$, and/or W are achiral in the synthetic intermediate, there is one or no asymmetric carbons in the molecule (multiple asymmetric carbon atoms are not present), and so diastereomers derived from asymmetric carbons are not generated, and purification and/or analysis of the intermediate is easier than synthesis with a mixture of diastereomers as an intermediate.

(3) The target compound may be synthesized with high purity of isomers by selecting reagents and/or reaction conditions having good selectivity.

(4) Applications to synthesize various derivatives having substituted butadiene structures characteristic to farnesenes are possible.

(5) A mixture of these isomers may be used as such for the purpose of biological activity. In such a case, an economic process for synthesizing may be advantageous, even with low selectivity.

(6) The target compound thus obtained is highly-stable, and may be stored at a room temperature. Purification may be carried out with a common purification method of organic compounds, such as distillation and/or silica gel chromatography.

EXAMPLES

The present invention will be described with reference to the following Examples. It should be noted that the present invention is not limited to or by the Examples.

Purities of raw materials, products, and intermediates were determined by gas chromatography (GC) and expressed as % GC, and determined by proton nuclear magnetic resonance ($^1$H-NMR) and expressed as % NMR. Isomer ratios of products and intermediates were the ratios of GC or $^1$H-NMR.

GC conditions: GC: Capillary gas chromatograph GC-14A (Shimadzu Corporation); column: 5% Ph-Me silicone, 0.25 mmϕ×25 m; carrier gas: He, detector: FID.

The yield is a calculated yield based on % GC or % NMR. Because raw materials used in reactions and products obtained in reactions do not always have a purity of 100%, a yield is calculated by the following equation: Calculated yield (%)={[(weight of a product obtained in a reaction×% GC)/molecular weight of a product]÷[(weight of a starting material in a reaction×% GC)/molecular weight of a starting material]}×100. Detection sensitivities in gas chromatography may differ among compounds, so that calculated yields may sometimes exceed 100%, particularly when raw materials or products are crude.

Purification was carried out to obtain samples for measuring spectra of the materials, where necessary.

Synthetic Examples: Synthesis of Primary Allylsulfone Compound of the Following General Formula (I)

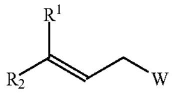

(I)

wherein $R^1$ and $R^2$ represent, independently of each other, a hydrogen atom or a linear, branched, or cyclic hydrocarbon group having 1 to 20 carbon atoms and optionally having an unsaturated bond(s), and W represents an arenesulfonyl group.

Synthetic Example 1: Synthesis of Geranyl p-Tolyl Sulfone (when $R^1$=$CH_3$, $R^2$=4-Methyl-3-Pentenyl Group, and W=Ts=p-Toluenesulfonyl Group in the General Formula (I))

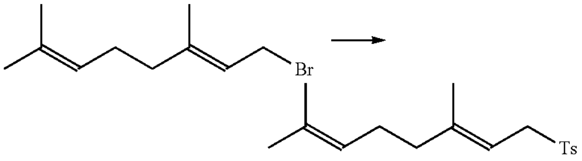

Geranyl bromide (55.0 g) was added dropwise to a mixture of sodium p-toluenesulphinate-tetrahydrate (80.0 g) and dimethylformamide (DMF; 250 ml) in a nitrogen atmosphere at 20° C. or lower, while occasionally cooled in an ice-water bath with stirring. The reaction mixture was stirred for 20 minutes at a room temperature. Water was added to the mixture, then and the mixture was extracted with n-hexane. The n-hexane solution was subjected to ordinary work-ups, i.e., washing, drying, and concentration to obtain geranyl p-tolyl sulfone (70.43 g, 93.8% GC, geometric isomer purity: E:Z=94.9:5.1, yield 89%).

Geranyl p-tolyl sulfone

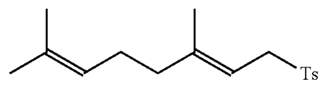 [SMILES: CC(C)=CCC/C(C)=C/CS(=O)(=O)c1ccc(C)cc1]

$C_{17}H_{24}O_2S$

Colorless Oil $^1$H-NMR (500 MHz, $CDCl_3$): δ=1.33 (3H, d, J=1.3 Hz), 1.58 (3H, d, J=0.8 Hz), 1.68 (3H, d, J=1.0 Hz), 2.00 (4H, br.s), 2.43 (3H, s), 3.78 (2H, d, J=7.8 Hz), 5.00-5.05 (1H, m), 5.17 (1H, dt-like, J=~1.3, ~7.9 Hz), 7.31 (2H, d-like, J=~8 Hz), 7.73 (2H, dt-like, J=~2, ~8 Hz) ppm.

Synthetic Example 2: Synthesis of Neryl p-Tolyl Sulfone (when $R^1$=4-Methyl-3-Pentenyl Group, $R^2$=$CH_3$, and W=Ts=p-Toluenesulfonyl Group in the General Formula (I))

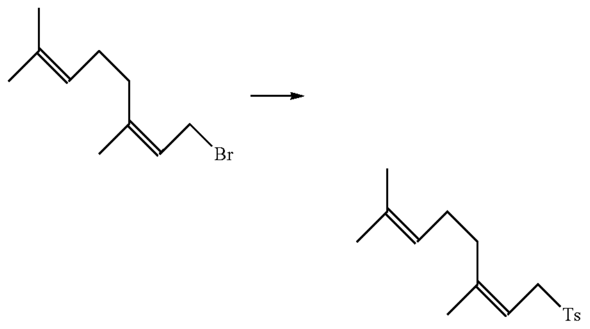

Neryl bromide (55.0 g) was added dropwise to a mixture of sodium p-toluenesulphinate-tetrahydrate (95.0 g) and DMF (250 ml) in a nitrogen atmosphere, while occasionally cooled in an ice-water bath with stirring at 22° C. or lower. After stirring the reaction mixture for 29 hours at a room temperature, water was added to the mixture, and the mixture was extracted with n-hexane. The n-hexane solution was subjected to ordinary work-ups, i.e., washing, drying, and concentration to obtain neryl p-tolyl sulfone (69.12 g, 94.3% GC, geometric isomer purity: Z:E=95.7:4.3, yield 84%).

Neryl p-Tolyl Sulfone

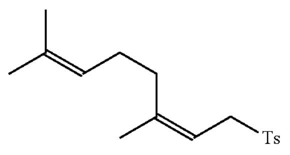 [SMILES: CC(C)=CCC/C(C)=C\CS(=O)(=O)c1ccc(C)cc1]

$C_{17}H_{24}O_2S$

Colorless Oil $^1$H-NMR (500 MHz, $CDCl_3$): δ=1.53 (3H, br.s), 1.64 (3H, d, J=1.2 Hz), 1.72 (3H, d, J=1.3 Hz), 1.74-1.79 (2H, m), 1.82-1.88 (2H, m), 2.43 (3H, s), 3.77 (2H, d-like, J=~8 Hz), 4.91-4.97 (1H, m), 5.18 (1H, t-like, J=~1.2, ~8 Hz), 7.31 (2H, d-like, J=~8 Hz), 7.73 (2H, dt-like, J=~2, ~8 Hz) ppm.

Synthetic Example 3: Synthesis of (E)-Cinnamyl Phenyl Sulfone (when $R^1$=H, $R^2$=pH=Phenyl Group, and W=Benzenesulfonyl Group in the General Formula (I))

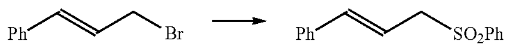

Cinnamyl bromide (25.0 g) was added dropwise to a mixture of sodium benzenesulphinate-dihydrate (95.0 g) and dimethylformamide (DMF; 250 ml) in a nitrogen atmosphere, while cooled in a water bath at 35° C. or lower with stirring. The reaction mixture was stirred for 48 hours at a room temperature. Water was added to the mixture, and then the mixture was extracted with diethyl ether. The diethyl ether solution was subjected to ordinary work-ups, i.e., washing, drying, and concentration to obtain (E)-cinnamyl phenyl sulfone (32.8 g, 99.3% NMR, including 0.7% DMF, quantitative yield).

(E)-Cinnamyl Phenyl Sulfone

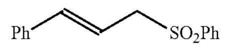

$C_{15}H_{14}O_2S$

Yellow Solid

IR (D-ATR): ν=3083, 3057, 3028, 2976, 2906, 1672, 1586, 1498, 1478, 1446, 1403, 1319, 1293, 1238, 1159, 1136, 1085, 1055, 1026, 999, 982, 908, 813, 760, 739, 698, 690 $cm^{-1}$.

$^1$H-NMR (500 MHz, $CDCl_3$): δ=3.95 (2H, dd, J=7.6, 1.1 Hz), 6.11 (1H, dt, J=15.9, 7.6 Hz), 6.37 (1H, d, J=15.9 Hz), 7.25-7.33 (5H, m), 7.52-7.57 (2H, m), 7.62-7.67 (1H, m), 7.87-7.91 (2H, m) ppm.

$^{13}$C-NMR (125 MHz, $CDCl_3$): δ=60.46, 115.07, 126.58, 128.488, 128.497, 128.64, 129.07, 133.75, 135.70, 138.34, 139.19 ppm.

GC-MS (EI, 70 eV): 51, 77, 91, 117 (base peak), 141, 164, 178, 193, 221, 258 ($M^+$).

Synthetic Examples: Synthesis of Primary Allylsulfone Compound of the Following General Formula (J)

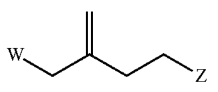

(J)

Synthetic Example 4: Synthesis of 4-Chloro-2-Methylenebutyl p-Tolyl Sulfone (when W=Ts=p-Toluenesulfonyl Group and Z=Cl in the General Formula (J))

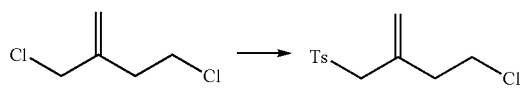

4-Chloro-2-chloromethyl-1-butene (12.51 g) was added dropwise to a mixture of sodium p-toluenesulphinate-tetrahydrate (22.60 g) and dimethylformamide (DMF; 120 ml) in a nitrogen atmosphere, while cooled in an ice-water bath at 25° C. or lower with stirring. The reaction mixture was stirred for 17 hours at a room temperature, sodium p-toluenesulphinate-tetrahydrate (5.05 g) was added to the reaction mixture, and then the reaction mixture was stirred for 3 more days. Water was added to the mixture, and the mixture was extracted with ethyl acetate. The ethyl acetate solution was subjected to ordinary work-ups, i.e., washing, drying, and concentration to obtain 4-chloro-2-methylenebutyl p-tolyl sulfone (23.85 g, 96.7 to 89% NMR, including 3.3 to 11% DMF, quantitative yield). A part of the reaction mixture was subjected to spectra measurement after removing DMF under vacuum.

4-Chloro-2-methylenebutyl p-tolyl sulfone

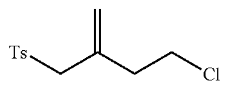 [SMILES: C=C(CCCl)CS(=O)(=O)c1ccc(C)cc1]

$C_{12}H_{15}ClO_2S$

Colorless Crystal

Melting point [inflection point of endothermic peak of DSC (differential scanning calorimeter); hereinafter the same shall apply]: 61.7° C.

IR (D-ATR): ν=2985, 2946, 2929, 1647, 1598, 1494, 1448, 1418, 1405, 1381, 1315, 1308, 1298, 1274, 1237, 1206, 1170, 1147, 1121, 1086, 1034, 1020, 938, 920, 816, 804, 780, 709, 650, 637, 611, 516, 454 $cm^{-1}$.

$^1H$-NMR (500 MHz, $CDCl_3$): δ=2.44 (3H, s), 2.68 (2H, t, J=6.7 Hz), 3.64 (2H, t, J=6.7 Hz), 3.78 (2H, s), 4.89 (1H, br.s), 5.15 (1H, br.s), 7.34 (2H, d-like, J=~8 Hz), 7.74 (2H, d-like, J=~8 Hz) ppm.

$^{13}C$-NMR (125 MHz, $CDCl_3$): δ=21.61, 37.91, 42.07, 62.57, 122.44, 128.44, 129.67, 133.60, 135.12, 144.84 ppm.

GC-MS (EI, 70 eV): 27, 41, 67 (base peak), 91, 105, 131, 155, 179, 194, 223, 241, 258 ($M^+$).

Synthetic Example 5: Synthesis of 4-Chloro-2-Methylenebutyl Phenyl Sulfone (when W=Benzenesulfonyl Group and Z═Cl in the General Formula (J))

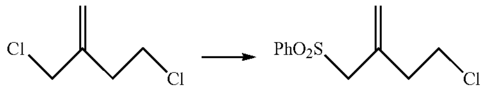

wherein Ph represents a phenyl group; hereinafter the same shall apply.

4-Chloro-2-chloromethyl-1-butene (41.2 g) was added dropwise to a mixture of sodium benzenesulphinate-dihydrate (71.0 g), tetrabutylammonium chloride (TBAC; 2.00 g), and acetonitrile (500 ml) in a nitrogen atmosphere at 50° C. with stirring for 35 minutes. The mixture was heated under reflux at 80 to 95° C. for 6 hours, and then stirred for 2 days at a room temperature. Water was added to the mixture, and the mixture was extracted with ethyl acetate. The ethyl acetate solution was subjected to ordinary work-ups, i.e., washing, drying, and concentration to obtain a crude product. The crude product was recrystallized from ethyl acetate-n-hexane to obtain 4-chloro-2-methylenebutyl phenyl sulfone (63.54 g, including TBAC 2.3% NMR, yield 89.4%). A part of the reaction mixture was purified by silica gel column chromatography and subjected to spectra measurement.

4-Chloro-2-Methylenebutyl Phenyl Sulfone

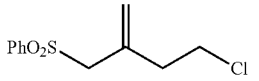

$C_{11}H_{13}ClO_2S$

Colorless Crystal

Melting point: 45.1° C.

IR (D-ATR): ν=3086, 2970, 2927, 1649, 1585, 1479, 1447, 1409, 1317, 1294, 1273, 1237, 1203, 1168, 1145, 1118, 1084, 1029, 999, 939, 922, 888, 797, 784, 757, 712, 690, 651, 615, 531 $cm^{-1}$.

$^1H$-NMR (500 MHz, $CDCl_3$): δ=2.70 (2H, t, J=6.7 Hz), 3.65 (2H, t, J=6.7 Hz), 3.81 (2H, s), 4.90 (1H, br.s), 5.16 (1H, br.s), 7.54-7.59 (2H, m), 7.64-7.68 (1H, m), 7.86-7.90 (2H, m) ppm.

$^{13}C$-NMR (125 MHz, $CDCl_3$): δ=37.92, 42.06, 62.55, 122.62, 128.48, 129.09, 133.49, 133.85, 138.07 ppm.

GC-MS (EI, 70 eV): 51, 77, 91, 117 (base peak), 141, 164, 178, 193, 221, 258 ($M^+$).

Examples: Synthesis of Secondary Allylsulfone Compound of the Following General Formula (G)

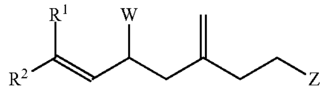

(G)

Example 1: Synthesis of (E)-1-chloro-7,11-dimethyl-3-methylene-6,10-dodecadien-5-yl p-tolyl sulfone (when $R^1$═$CH_3$, $R^2$=4-methyl-3-pentenyl group, W=Ts=p-toluenesulfonyl group, and Z═Cl in the general formula (G))

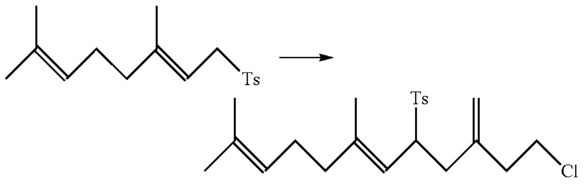

A solution of 2.80 M n-butyllithium in n-hexane (13 ml) was added dropwise to a mixture of geranyl p-tolyl sulfone (11.3 g, 93.8% GC) synthesized in the aforesaid Synthetic Example 1 and tetrahydrofuran (THF; 80 ml) in a nitrogen atmosphere, while cooled to −60° C. or lower with stirring. The reaction mixture was stirred for 30 minutes at this temperature, and then a mixture of 2-bromomethyl-4-chloro-1-butene (7.0 g, 95.0% NMR) and THF (25 ml) were added dropwise for 20 minutes. The reaction temperature was gradually raised to a room temperature and stirred for 15 hours. The reaction mixture was ice-cooled, and the reaction was quenched by adding dilute hydrochloric acid. The reaction mixture was extracted with ethyl acetate. The ethyl acetate solution was subjected to ordinary work-ups, i.e., washing, drying, and concentration to obtain (E)-1-chloro-7,11-dimethyl-3-methylene-6,10-dodecadien-5-yl p-tolyl sulfone (15.19 g, quantitative yield).

(E)-1-Chloro-7,11-dimethyl-3-methylene-6,10-dodecadien-5-yl p-tolyl sulfone

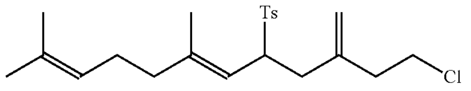 [SMILES: C=C(CCCl)CC(/C=C(\C)CCC=C(C)C)S(=O)(=O)c1ccc(C)cc1]

$C_{22}H_{31}ClO_2S$

Yellowish Oil

IR (D-ATR): ν=2965, 2923, 1649, 1597, 1445, 1377, 1312, 1301, 1288, 1145, 1086, 898, 815, 739, 661, 584 $cm^{-1}$.

$^1$H-NMR (500 MHz, $CDCl_3$): δ=1.18 (3H, d, J=1.3 Hz), 1.58 (3H, s), 1.67 (3H, s), 1.92-1.98 (4H, m), 2.32 (1H, dd, J=11.4, 14.3 Hz), 2.40 (2H, t, J=7.2 Hz), 2.43 (3H, s), 2.93 (1H, br.d, J=~13 Hz), 3.52-3.61 (2H, m), 3.84-3.91[1H, m (ddd-like)], 4.84 (1H, s), 4.87 (1H, s), 4.87-4.92 (1H, br.d-like), 4.97-5.03 (1H, m), 7.30 (2H, d-like, J=~8 Hz), 7.70 (2H, d-like, J=~8 Hz) ppm.

$^{13}$C-NMR (125 MHz, $CDCl_3$): δ=16.42, 17.63, 21.61, 25.64, 26.03, 33.87, 38.83, 39.60, 42.12, 63.34, 114.96, 117.11, 123.49, 129.27, 129.35, 131.91, 134.62, 140.74, 144.45, 145.59 ppm.

Example 2: Synthesis of (Z)-1-chloro-7,11-dimethyl-3-methylene-6,10-dodecadien-5-yl p-tolyl sulfone (when $R^1$=4-methyl-3-pentenyl group, $R^2$=$CH_3$, W=Ts=p-Toluenesulfonyl Group, and Z=Cl in the General Formula (G))

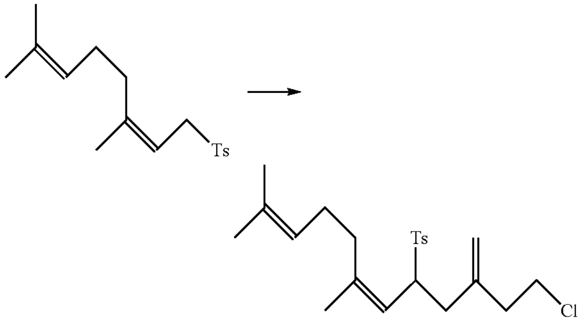

A solution of 2.80 M n-butyllithium in n-hexane (55.4 ml) was added dropwise to a mixture of neryl p-tolyl sulfone (48.1 g, 94.3% GC) synthesized in the aforesaid Synthetic Example 2 and tetrahydrofuran (THF; 250 ml) in a nitrogen atmosphere, while cooled to −60° C. or lower with stirring. The reaction mixture was stirred for 45 minutes at this temperature, and then 2-bromomethyl-4-chloro-1-butene (30.0 g, 96.9% GC) was added dropwise for 40 minutes. The reaction mixture was stirred for 2 hours at this temperature. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration to obtain a 85.8:14.1 ($^1$H-NMR) mixture (67.85 g) of (Z)-1-chloro-7,11-dimethyl-3-methylene-6,10-dodecadien-5-yl p-tolyl sulfone: (Z)-1-(2,6-dimethyl-1,5-heptadienyl)-3-methylene-cyclopentan-1-yl p-tolyl sulfone (target compound purity calculated yield 86%).

The by-product, (Z)-1-(2,6-dimethyl-1,5-heptadienyl)-3-methylenecyclopentan-1-yl p-tolyl sulfone, resulted from an excess base causing intramolecular alkylation and cyclization of sulfone anion from the target compound, and suggests that the use of an excess base is to be avoided.

A part of the mixture was purified by silica gel column chromatography and subjected to spectra measurement.

(Z)-1-Chloro-7,11-dimethyl-3-methylene-6,10-dodecadien-5-yl p-tolyl sulfone

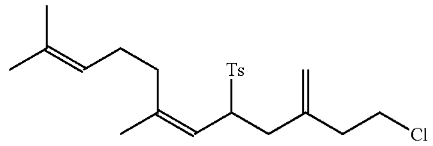 [SMILES: C=C(CCCl)CC(/C=C(/C)CCC=C(C)C)S(=O)(=O)c1ccc(C)cc1]

$C_{22}H_{31}CO_2S$

Yellowish Oil

IR (D-ATR): ν=2966, 2917, 2858, 1649, 1597, 1445, 1377, 1312, 1301, 1288, 1145, 1086, 901, 815, 738, 661, 580 $cm^{-1}$.

$^1$H-NMR (500 MHz, $CDCl_3$): δ=1.46-1.52 (1H, m), 1.53 (3H, br.s), 1.64 (3H, d, J=~1 Hz), 1.68 (3H, d, J=~1 Hz), 1.68-1.83 (3H, m), 2.28 (1H, dd, J=11.1, 14.1 Hz), 2.41 (2H, t, J=7.3 Hz), 2.43 (3H, s), 2.89 (1H, dd, J=2.4, 14.1 Hz), 3.51-3.60 (2H, m), 3.88 (1H, dt, J=3.1, 10.7 Hz), 4.87-4.94 (4H, m), 7.29-7.33 (2H, d-like, J=~8 Hz), 7.68-7.72 (2H, d-like, J=~8 Hz) ppm.

$^{13}$C-NMR (125 MHz, $CDCl_3$): δ=17.63, 21.61, 23.21, 25.60, 25.83, 32.14, 34.14, 38.84, 42.14, 63.35, 115.39, 117.41, 123.46, 129.25, 129.38, 132.04, 134.67, 140.80, 144.48, 145.73 ppm.

Example 3: Synthesis of (E)-7-chloro-5-methylene-1-phenyl-1-hepten-3-yl phenyl Sulfone (when $R^1$=H, $R^2$=pH, W=Benzenesulfonyl Group, and Z=Cl in the General Formula (G))

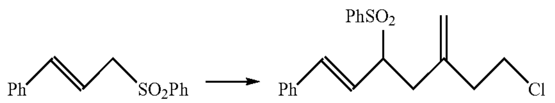

A solution of 2.80 M n-butyllithium in n-hexane (23.5 ml) was added dropwise to a mixture of (E)-cinnamyl phenyl sulfone (17.4 g, 99.3% GC) synthesized in the aforesaid Synthetic Example 3 and tetrahydrofuran (THF; 150 ml) in a nitrogen atmosphere, while cooled to −60° C. or lower with stirring. The reaction mixture was stirred for 1 hour at this temperature, and then 2-bromomethyl-4-chloro-1-butene (13.53 g, 91% GC) was added dropwise for 40 minutes. The reaction mixture was gradually raised to a room temperature and stirred for 12 hours. The reaction mixture was ice-cooled, and the reaction was quenched by adding an aqueous solution of ammonium chloride to the reaction mixture. The reaction mixture was extracted with diethyl ether. The diethyl ether solution was subjected to ordinary work-ups, i.e., washing, drying, and concentration, and then purified by silica gel column chromatography to obtain (E)-7-chloro-5-methylene-1-phenyl-1-hepten-3-yl phenyl sulfone (14.91 g, yield 64%).

(E)-7-Chloro-5-methylene-1-phenyl-1-hepten-3-yl Phenyl Sulfone

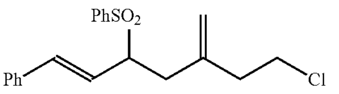

$C_{20}H_{21}ClO_2S$
Yellowish Oil

IR (D-ATR): ν=3060, 3027, 2961, 1648, 1584, 1495, 1447, 1305, 1243, 1209, 1145, 1084, 968, 912, 755, 735, 690, 600 $cm^{-1}$.

$^1$H-NMR (500 MHz, $CDCl_3$): δ=2.44 (2H, t, J=7.1 Hz), 2.52 (1H, dd-like, J=14.5, 11.5 Hz), 3.01 (1H, d-like, J=14.5 Hz), 3.53-3.63 (2H, m), 3.78-3.84 (1H, m), 4.92 (1H, s), 4.94 (1H, s), 5.86 (1H, dd, J=15.9, 9.4 Hz), 6.20 (1H, d, J=15.9 Hz), 7.19-7.34 (5H, m), 7.48-7.54 (2H, m), 7.61-7.65 (1H, m), 7.82-7.87 (2H, m) ppm.

$^{13}$C-NMR (125 MHz, $CDCl_3$): δ=33.58, 38.54, 42.10, 67.86, 115.80, 120.59, 126.55, 128.56, 128.62, 128.90, 129.26, 133.80, 135.64, 137.08, 138.45, 140.20 ppm.

Examples: Synthesis of Secondary Allylsulfone Compound of the Following General Formula (H)

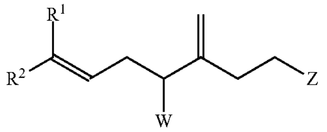
(H)

Example 4: Synthesis of (E)-1-chloro-7,11-dimethyl-3-methylene-6,10-dodecadien-4-yl phenyl sulfone (when $R^1$=$CH_3$, $R^2$=4-methyl-3-pentenyl group, W=benzenesulfonyl Group, and Z=Cl in the General Formula (H))

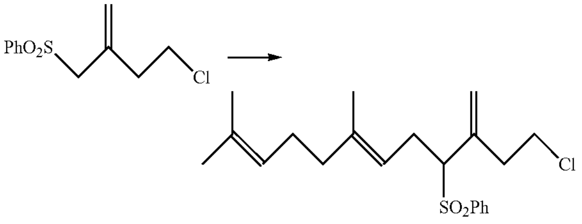

A solution of 2.80 M n-butyllithium in n-hexane (70.0 ml) was added dropwise to a mixture of 4-chloro-2-methylenebutyl phenyl sulfone (43.21 g, 99% NMR) synthesized in the aforesaid Synthetic Example 5 and tetrahydrofuran (THF; 500 ml) in a nitrogen atmosphere, while cooled to −65° C. or lower with stirring. The reaction mixture was stirred for 1 hour at this temperature, and then geranyl bromide 42.6 g was added dropwise for 30 minutes. The reaction mixture was gradually raise to a room temperature and stirred for 30 hours. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration, and then purified by silica gel column chromatography to obtain (E)-1-chloro-7,11-dimethyl-3-methylene-6,10-dodecadien-4-yl phenyl sulfone (36.4 g, yield 54%).

(E)-1-Chloro-7,11-dimethyl-3-methylene-6,10-dodecadien-4-yl phenyl sulfone

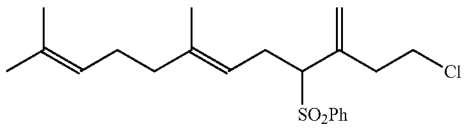

$C_{21}H_{29}ClO_2S$
Yellowish Oil

IR (D-ATR): ν=2965, 2918, 2856, 1644, 1585, 1447, 1377, 1305, 1205, 1146, 1084, 923, 823, 755, 721, 670, 615, 546 $cm^{-1}$.

$^1$H-NMR (500 MHz, $CDCl_3$): δ=1.54 (3H, br.s), 1.56 (3H, br.s), 1.65 (3H, br.s), 1.89-2.03 (4H, m), 2.43-2.59 (3H, m), 2.75-2.81 (1H, m), 3.47-3.59 (3H, m), 4.90-4.95 (1H, m), 4.98-5.03 (1H, m), 5.10 (1H, s-like), 5.22 (1H, s-like), 7.52-7.57 (2H, m), 7.63-7.67 (1H, m), 7.84-7.88 (2H, m) ppm.

$^{13}$C-NMR (125 MHz, $CDCl_3$): δ=16.20, 17.64, 25.65, 26.21, 26.38, 38.29, 39.52, 41.79, 70.56, 118.08, 120.42, 123.81, 128.87, 129.27, 131.63, 133.72, 137.08, 137.29, 139.06 ppm.

Example 5: Synthesis of (Z)-1-chloro-7,11-dimethyl-3-methylene-6,10-dodecadien-4-yl p-tolyl sulfone (when $R^1$=4-methyl-3-pentenyl group, $R^2$=$CH_3$, W=p-toluenesulfonyl Group, and Z=Cl in the General Formula (H))

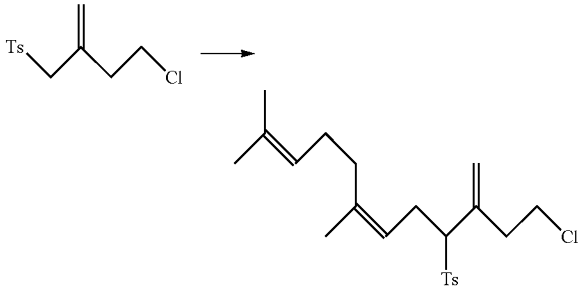

A solution of 2.80 M n-butyllithiumin n-hexane (28.5 ml) was added dropwise to a mixture of 4-chloro-2-methylenebutyl p-tolyl sulfone (17.1 g, 96.0% NMR) synthesized in the aforesaid Synthetic Example 4 and tetrahydrofuran (250 ml) in a nitrogen atmosphere, while cooled to −60° C. or lower with stirring. The reaction mixture was stirred for 30 minutes at this temperature, and then neryl bromide (14.60 g, Z 95.1% NMR) was added dropwise for 10 minutes. The reaction mixture was gradually raised to a room temperature and stirred for 15 hours. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration, and then purified by silica gel column chromatography to obtain (Z)-1-chloro-7,11-dimethyl-3-methylene-6,10-dodecadien-4-yl p-tolyl sulfone (19.1 g, yield 76%).

(Z)-1-Chloro-7,11-dimethyl-3-methylene-6,10-dodecadien-4-yl p-tolyl sulfone

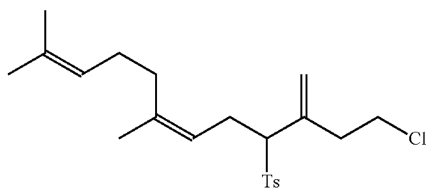 [SMILES: C=C(CCCl)C(C/C=C(/C)CCC=C(C)C)S(=O)(=O)c1ccc(C)cc1]

$C_{22}H_{31}ClO_2S$

Colorless Oil

IR (D-ATR): ν=2965, 2923, 2858, 1643, 1597, 1448, 1377, 1315, 1301, 1290, 1145, 1085, 922, 816, 735, 667, 593 $cm^{-1}$.

$^1$H-NMR (500 MHz, $CDCl_3$): δ=1.59 (3H, br.s), 1.63 (3H, d, J=~1.3 Hz), 1.67 (3H, br.s), 1.87-2.03 (4H, m), 2.41-2.58 (3H, m), 2.45 (3H, s), 2.74-2.81 (1H, m), 3.43-3.60 (3H, m), 4.93 (1H, t-like, J=~8 Hz), 4.99-5.03 (1H, m), 5.11 (1H, s-like), 5.23 (1H, s-like), 7.33 (2H, dd-like, J=~8.5, ~0.6 Hz), 7.72 (2H, dt-like, J=~8.5, ~2 Hz) ppm.

$^{13}$C-NMR (125 MHz, $CDCl_3$): δ=17.63, 21.63, 23.28, 25.73, 26.15, 26.25, 31.95, 38.56, 41.81, 70.72, 118.94, 120.28, 123.78, 129.28, 129.49, 131.94, 134.41, 137.12, 139.04, 144.69 ppm.

Example 6: Synthesis of 1-chloro-7-methyl-3-methylen-6-octen-4-yl p-tolyl sulfone (when $R^1$=$R^2$=$CH_3$, W=p-toluenesulfonyl group, and Z=Cl in the general formula (H))

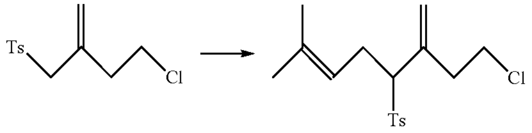

A solution of 2.80 M n-butyllithium in n-hexane (7.35 ml) was added dropwise to a mixture of 4-chloro-2-methylenebutyl p-tolyl sulfone (5.00 g, 96.7% NMR) synthesized in the aforesaid Synthetic Example 5 and tetrahydrofuran (80 ml) in a nitrogen atmosphere, while cooled to −60° C. or lower with stirring. The reaction mixture was stirred for 40 minutes at this temperature, and then prenyl bromide (1-bromo-3-methyl-2-butene) (3.35 g) was added dropwise for 5 minutes. The reaction mixture was gradually raised to a room temperature and stirred for 16 hours. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration, and then purified by silica gel column chromatography to obtain 1-chloro-7-methyl-3-methylen-6-octen-4-yl p-tolyl sulfone (5.35 g, 97.4 to 98.7% GC (a purity written as a range means that the purities of the multiple fractions obtained were in the range; hereinafter the same shall apply for purities written % GC and % NMR), including 1.1 to 2.2% of corresponding bromide, 1-bromo-7-methyl-3-methylen-6-octen-4-yl p-tolyl sulfone, yield 88%).

1-Chloro-7-methyl-3-methylen-6-octen-4-yl p-tolyl sulfone

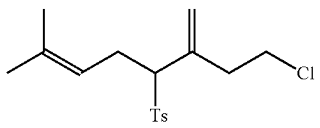 [SMILES: C=C(CCCl)C(CC=C(C)C)S(=O)(=O)c1ccc(C)cc1]

$C_{17}H_{23}ClO_2S$

Yellowish Oil

IR (D-ATR): ν=2967, 2917, 1643, 1597, 1450, 1378, 1315, 1301, 1289, 1144, 1086, 923, 816, 709, 667, 593 $cm^{-1}$.

$^1$H-NMR (500 MHz, $CDC_3$): δ=1.55 (3H, br.s), 1.63 (3H, d-like, J=~1.2 Hz), 2.42-2.57 (3H, m), 2.44 (3H, s), 2.73-2.79 (1H, m), 3.47-3.52 (2H, m), 3.53-3.58 (1H, m), 4.88-4.93 (1H, m), 5.08 (1H, s-like), 5.21 (1H, s-like), 7.32 (2H, dd-like, J=~8, ~1 Hz), 7.72 (2H, dt-like, J=~8, ~2 Hz) ppm.

$^{13}$C-NMR (125 MHz, $CDCl_3$): δ=17.85, 21.62, 25.63, 38.26, 38.38, 41.83, 70.49, 118.36, 120.25, 129.27, 129.48, 134.32, 135.32, 137.23, 144.69 ppm.

1-Bromo-7-methyl-3-methylen-6-octen-4-yl p-tolyl sulfone

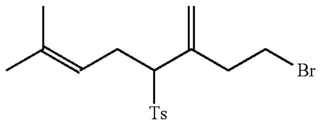 [SMILES: C=C(CCBr)C(CC=C(C)C)S(=O)(=O)c1ccc(C)cc1]

$C_{17}H_{23}BrO_2S$

GC-MS (EI, 70 eV): 41, 79, 107 (base peak), 135, 170, 215, 217.

GC-MS (CI, isobutane): 157, 215, 371, 373 ($M+H^+$, base peak).

Example 7: Synthesis of 1-chloro-7-methyl-3-methylen-6-octen-4-yl phenyl sulfone (when $R^1$=$R^2$=$CH_3$, W=benzenesulfonyl group, and Z=Cl in the general formula (H))

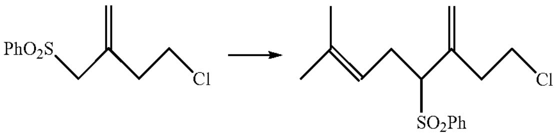

A solution of 2.76 M n-butyllithium in n-hexane (150 ml) was added dropwise for 20 minutes to a mixture of 4-chloro-2-methylenebutyl phenyl sulfone (91.4 g, 96% NMR) synthesized by a process similar to the aforesaid Synthetic Example 5 and tetrahydrofuran (800 ml) in a nitrogen atmosphere, while cooled to −60° C. or lower with stirring. The reaction mixture was stirred for 35 minutes at this temperature, and then prenyl bromide (1-bromo-3-methyl-2-butene) (67.0 g) was added dropwise for 20 minutes. The reaction mixture was gradually raised to a room temperature and stirred for 16.5 hours. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration to obtain 1-chloro-7-methyl-3-methylen-6-octen-4-yl phenyl sulfone (116.29 g, yield 99%).

1-Chloro-7-methyl-3-methylen-6-octen-4-yl phenyl sulfone

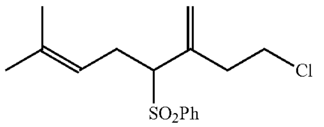

$C_{16}H_{21}ClO_2S$
Yellowish Oil

IR (D-ATR): ν=3064, 2965, 2916, 1673, 1643, 1585, 1447, 1377, 1304, 1244, 1146, 1085, 923, 755, 720, 690, 615 $cm^{-1}$.

$^1$H-NMR (500 MHz, $CDCl_3$): δ=1.54 (3H, br.s), 1.63 (3H, d-like, J=~1 Hz), 2.42-2.58 (3H, m), 2.73-2.82 (1H, m), 3.47-3.59 (3H, m), 4.88-4.93 (1H, m), 5.10 (1H, s-like), 5.22 (1H, s-like), 7.52-7.58 (2H, m), 7.62-7.67 (1H, m), 7.83-7.89 (2H, m) ppm.

$^{13}$C-NMR (125 MHz, $CDCl_3$): δ=17.84, 25.64, 26.35, 38.33, 41.78, 70.49, 118.24, 120.41, 128.86, 129.25, 133.71, 135.47, 137.09, 137.32 ppm.

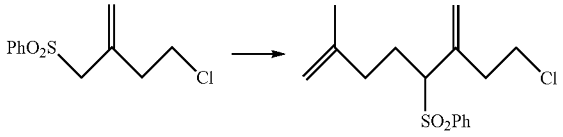

Example 8: Synthesis of (E)-7-chloro-5-methylene-1-phenyl-1-hepten-4-yl p-tolyl sulfone (when $R^1$=H, $R^2$=Ph=$C_6H_5$, W=p-toluenesulfonyl group, and Z=Cl in the general formula (H))

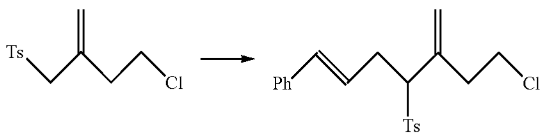

A solution of 2.80 M n-butyllithium in n-hexane (26.4 ml) was added dropwise for 15 minutes to a mixture of 4-chloro-2-methylenebutyl p-tolyl sulfone (17.4 g, 97% NMR) synthesized in the aforesaid Synthetic Example 4 and tetrahydrofuran (150 ml) in a nitrogen atmosphere, while cooled to −60° C. or lower with stirring. The reaction mixture was stirred for 1 hour at this temperature, and then cinnamyl bromide (14.6 g) was added dropwise for 15 minutes. The reaction mixture was gradually raised to a room temperature and stirred for 16 hours. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration to obtain crude (E)-7-chloro-5-methylene-1-phenyl-1-hepten-4-yl p-tolyl sulfone (26.03 g, quantitative yield). This crude product had sufficient purity, and was used as such as a starting material in a subsequent step.

7-Chloro-5-methylene-1-phenyl-1-hepten-4-yl p-tolyl sulfone

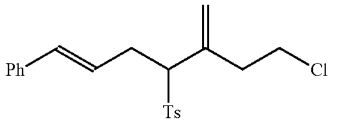 [SMILES: C=C(CCCl)C(C/C=C/c1ccccc1)S(=O)(=O)c1ccc(C)cc1]

$C_{21}H_{23}ClO_2S$
Colorless Oil

IR (D-ATR): ν=3026, 2959, 2923, 2869, 1643, 1597, 1494, 1447, 1313, 1302, 1290, 1144, 1085, 967, 923, 816, 743, 708, 693, 669, 606, 588 $cm^{-1}$.

$^1$H-NMR (500 MHz, $CDCl_3$): δ=2.45 (3H, s), 2.48-2.62 (2H, m), 2.68-2.76 (1H, m), 2.96-3.02 (1H, m), 3.51-3.61 (2H, m), 3.66 (1H, dd, J=4.0, 11.4 Hz), 5.14 (1H, s), 5.27 (1H, s-like), 5.99 (1H, dt, J=15.7, 7.2 Hz), 6.42 (1H, dt-like, J=15.7, ~1.2 Hz), 7.18-7.22 (1H, m), 7.26-7.29 (4H, m), 7.34 (2H, d-like, J=~8.5, ~0.6 Hz), 7.75 (2H, dt-like, J=~8.5, ~1.9 Hz) ppm.

$^{13}$C-NMR (125 MHz, $CDCl_3$): δ=21.65, 31.32, 38.32.41, 84, 70.37, 120.67, 124.06, 126.14, 127.54, 128.52, 129.37, 129.58, 133.53, 134.02, 136.69, 136.89, 144.93 ppm.

Synthetic Example 6: Synthesis of 1-chloro-3-methylenedodecan-4-yl p-tolyl sulfone

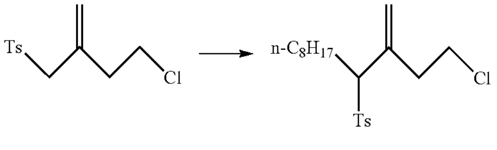

A solution of 2.76 M n-butyllithium in n-hexane (65.5 ml) was added dropwise for 30 minutes to a mixture of 4-chloro-2-methylenebutyl p-tolyl sulfone (41.58 g, ~97% NMR) synthesized by a process similar to the aforesaid Synthetic Example 4 and tetrahydrofuran (500 ml) in a nitrogen atmosphere, while cooled to −60° C. or lower with stirring. The reaction mixture was stirred for 40 minutes at this temperature, and then 1-bromooctane (34.8 g) was added dropwise for 10 minutes. The reaction mixture was gradually raised to a room temperature and stirred for 16 hours. The reaction mixture was ice-cooled, and the reaction was quenched by adding an aqueous solution of ammonium chloride. The reaction mixture was extracted with ethyl acetate. The ethyl acetate solution was subjected to ordinary work-ups, i.e., washing, drying, and concentration, and then purified by silica gel column chromatography to obtain 1-chloro-3-methylenedodecan-4-yl p-tolyl sulfone (51.1 g, yield 86%).

1-Chloro-3-methylenedodecan-4-yl p-tolyl sulfone

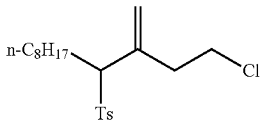

$C_{20}H_{31}ClO_2S$

Colorless Solid

Melting point: 52.5° C.

IR (D-ATR): ν=2954, 2925, 2855, 1642, 1597, 1494, 1456, 1379, 1313, 1302, 1289, 1145, 1086, 1019, 923, 815, 708, 667 $cm^{-1}$.

$^1$H-NMR (500 MHz, $CDCl_3$): δ=0.86 (3H, t, J=7.0 Hz), 1.13-1.37 (12H, m), 1.72-1.82 (1H, m), 1.98-2.08 (1H, m), 2.44 (3H, s), 2.45-2.53 (1H, m), 2.56-2.66 (1H, m), 3.50 (1H, dd, J=11.7, 3.5 Hz), 3.56 (1H, dt-like, J=11.7, 3.5 Hz), 3.61 (1H, ddd, J=11.0, 7.5, 6.3 Hz), 5.01 (1H, s), 5.19 (1H, t-like, J=~1.4 Hz), 7.32 (2H, dd-like, J=0.6, 8.6), 7.70 (2H, dt-like, J=8.2, ~2 Hz) ppm.

$^{13}$C-NMR (125 MHz, $CDCl_3$): δ=14.07, 21.64, 22.59, 26.49, 27.12, 29.09, 29.15, 29.19, 31.74, 37.83, 41.90, 71.04, 119.92, 129.29, 129.46, 134.18, 137.33, 144.66 ppm.

Examples: Synthesis of Halide Compound of the Following General Formula (D)

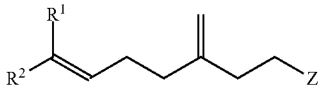

(D)

Example 9: Synthesis of (E)-12-chloro-2,6-dimethyl-10-methylene-2,6-dodecadiene (when $R^1$=$CH_3$, $R^2$=4-methyl-3-pentenyl group, and Z=Cl in the general formula (D))

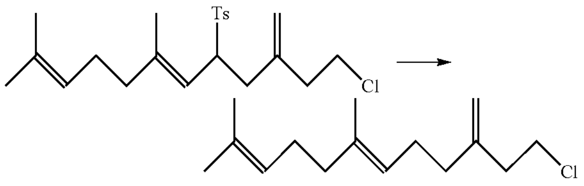

A solution of 1.0 M lithium triethylborohydride (Super-Hydride®) in tetrahydrofuran (61 ml) was added dropwise for 35 minutes to a mixture of (E)-1-chloro-7,11-dimethyl-3-methylene-6,10-dodecadien-5-yl p-tolyl sulfone (20.0 g, ~100% NMR) synthesized by a process similar to the aforesaid Example 1, 1,3-bis(diphenylphosphino)propane palladium(II) chloride ($PdCl_2(dppp)_2$, 1.50 g) and tetrahydrofuran (200 ml) in a nitrogen atmosphere under ice cooling with stirring. The reaction mixture was stirred for 2 hours at this temperature, an aqueous solution (75 g) of 12.5% sodium hydroxide was added dropwise, and then 35% aqueous hydrogen peroxide (11.3 g) was added dropwise. The reaction mixture was stirred for 20 minutes under ice cooling. The reaction mixture was filtered off through Celite©, and then an organic layer was fractionated. The organic layer was subjected to ordinary work-ups, i.e., washing, drying, and concentration, and then purified by silica gel column chromatography to obtain (E)-12-chloro-2,6-dimethyl-10-methylene-2,6-dodecadiene (9.22 g, 80.4 to 97.6% GC, 97.2 to 99.1% E, yield 72%).

(E)-12-Chloro-2,6-dimethyl-10-methylene-2,6-dodecadiene

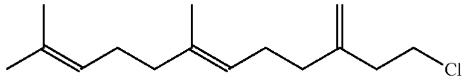 [SMILES: C=C(CCCl)CC/C=C(\C)CCC=C(C)C]

$C_{15}H_{25}Cl$

Colorless Oil

IR (D-ATR): ν=2965, 2925, 2855, 1646, 1448, 1377, 1325, 1300, 1242, 1152, 1108, 984, 895, 834, 739, 661 $cm^{-1}$.

$^1$H-NMR (500 MHz, $CDCl_3$): δ=1.61 (6H, br.s), 1.68 (3H, br.s.), 1.96-2.01 (2H, m), 2.03-2.11 (4H, m), 2.12-2.17 (2H, m), 2.50 (2H, t, J=7.5 Hz), 3.61 (2H, t, J=7.5 Hz), 4.82 (1H, br.s), 4.88 (1H, br.s), 5.07-5.15 (2H, m) ppm.

$^{13}$C-NMR (125 MHz, $CDCl_3$): δ=16.02, 17.67, 25.67, 26.17, 26.65, 35.82, 39.16, 39.65, 42.80, 111.67, 123.54, 124.26, 131.32, 135.55, 145.55 ppm.

GC-MS (EI, 70 eV): 27, 41, 55, 69 (base peak), 81, 93, 109, 121, 136, 169, 197, 240 ($M^+$).

Example 10: Synthesis (1) of (Z)-12-chloro-2,6-dimethyl-10-methylene-2,6-dodecadiene (when $R^1$=4-methyl-3-pentenyl group, $R^2$=$CH_3$, and Z=Cl in the general formula (D))

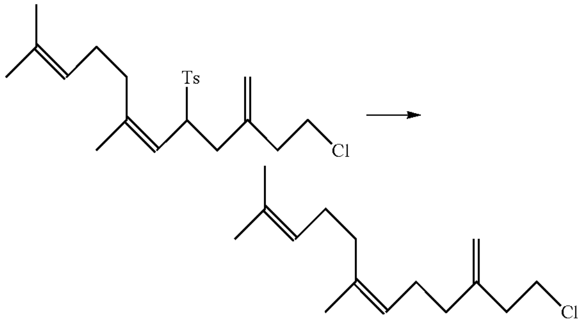

A solution of 1.7 M lithium triethylborohydride in tetrahydrofuran (29.8 ml) was added dropwise for 1 hour to a mixture of (Z)-1-chloro-7,11-dimethyl-3-methylene-6,10-dodecadien-5-yl p-tolyl sulfone (20.0 g, 85.8% NMR) synthesized in the aforesaid Example 2, 1,3-bis(diphenylphosphino)propane palladium(II) chloride (2.99 g), and tetrahydrofuran (250 ml) in a nitrogen atmosphere under ice cooling with stirring. The reaction temperature was gradually raised to a room temperature and stirred for 14 hours. The reaction mixture was ice-cooled, an aqueous solution (70 g) of 12.5% sodium hydroxide was added dropwise, and then 35% aqueous hydrogen peroxide (10 g) was added dropwise. The reaction mixture was extracted with diethyl ether. The diethyl ether solution was subjected to ordinary work-ups, i.e., washing, drying, and concentration, and then purified by silica gel column chromatography to obtain the starting material, (Z)-1-chloro-7,11-dimethyl-3-methylene-6,10-dodecadien-5-yl p-tolyl sulfone (7.81 g, recovery yield 43.1%), and the target compound, (Z)-12-chloro-2,6-dimethyl-10-methylene-2,6-dodecadiene (3.05 g, 99.3% GC, 91.5% Z, yield 29%; yield with recovery consideration 53%).

(Z)-12-Chloro-2,6-dimethyl-10-methylene-2,6-dodecadiene

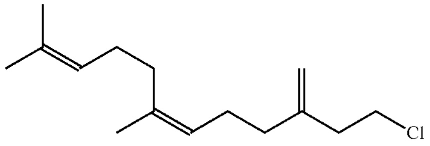 [SMILES: C=C(CCCl)CC/C=C(/C)CCC=C(C)C]

$C_{15}H_{25}Cl$

Colorless Oil

IR (D-ATR): ν=2964, 2927, 2856, 1646, 1449, 1376, 1325, 1242, 1152, 1109, 984, 895, 831, 738, 661 $cm^{-1}$.

$^1$H-NMR (500 MHz, $CDCl_3$): δ=1.62 (3H, br.s), 1.69 (6H, s-like), 1.97-2.10 (6H, m), 2.10-2.17 (2H, m), 2.49 (2H, t, J=7.5 Hz), 3.61 (2H, t, J=7.5 Hz), 4.82 (1H, br.s), 4.87 (1H, br.s), 5.09-5.15 (2H, m) ppm.

$^{13}$C-NMR (125 MHz, $CDCl_3$): δ=17.62, 23.34, 25.71, 26.08, 26.54, 31.98, 36.10, 39.19, 42.78, 111.63, 124.21, 124.33, 131.63, 135.74, 145.57 ppm.

GC-MS (EI, 70 eV): 27, 41, 53, 69 (base peak), 81, 93, 109, 129, 156, 169, 197, 240 ($M^+$).

Example 11: Synthesis (2) of (Z)-12-chloro-2,6-dimethyl-10-methylene-2,6-dodecadiene (when $R^1$=4-methyl-3-pentenyl group, $R^2$=$CH_3$, and Z=Cl in the general formula (D))

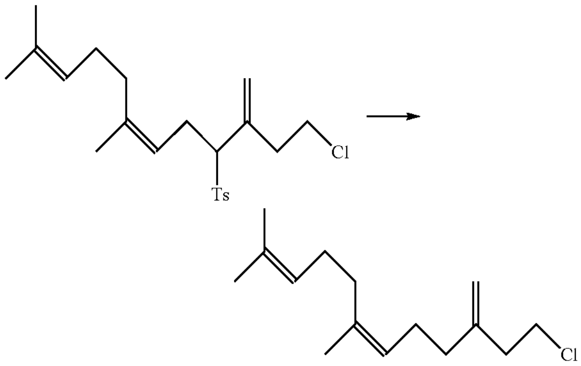

A solution of 1.7 M lithium triethylborohydride in tetrahydrofuran (3.51 ml) was added dropwise for 1 hour to a mixture of (Z)-1-chloro-7,11-dimethyl-3-methylene-6,10-dodecadien-4-yl p-tolyl sulfone (1.95 g, 95% NMR) synthesized in the aforesaid Example 5, 1,3-bis(diphenylphosphino)propane palladium(II) chloride (0.145 g), and tetrahydrofuran (40 ml) in a nitrogen atmosphere under ice cooling with stirring. The reaction mixture was stirred for 2.5 hours under ice cooling, an aqueous solution (7.4 g) of 12.5% sodium hydroxide was added dropwise, and then 35% aqueous hydrogen peroxide (1.2 g) was added dropwise. The reaction mixture was extracted with diethyl ether. The diethyl ether solution was subjected to ordinary work-ups, i.e., washing, drying, and concentration, and then purified by silica gel column chromatography. A 8:38:54 mixture of target compound (Z)-12-chloro-2,6-dimethyl-10-methylene-2,6-dodecadiene:target compound isomer (6Z,9E)-12-chloro-2,6,10-trimethyl-2,6,9-dodecatriene:target compound isomer (6Z,9Z)-12-chloro-2,6,10-trimethyl-2,6,9-dodecatriene (isomer total yield 92%) was obtained.

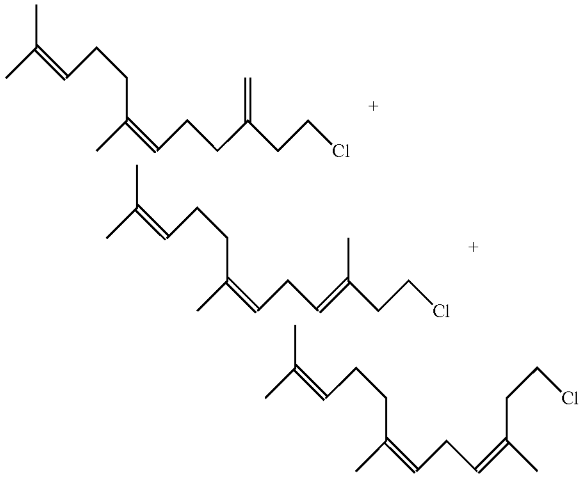

The results of this example suggest that, as starting materials to obtain the target compound, (Z)-12-chloro-2,6-dimethyl-10-methylene-2,6-dodecadiene, a position-5 sulfone compound having sulfone at an allyl position of a trisubstituted double bond such as (Z)-1-chloro-7,11-dimethyl-3-methylene-6,10-dodecadien-5-yl p-tolyl sulfone mentioned above has excellent stereospecificity and reaction selectivity, whereas a position-4 sulfone compound having sulfone at an allyl position of an exo-methylene group such as (Z)-1-chloro-7,11-dimethyl-3-methylene-6,10-dodecadien-4-yl p-tolyl sulfone of this example may have poor stereospecificity and reaction selectivity due to desulfonation during allylic rearrangement, specifically, desulfonation as the double bond rearranges from the exo-position toward the trisubstituted side.

Synthetic Example 7: Synthesis of 2-(2-chloroethyl)-1-undecene

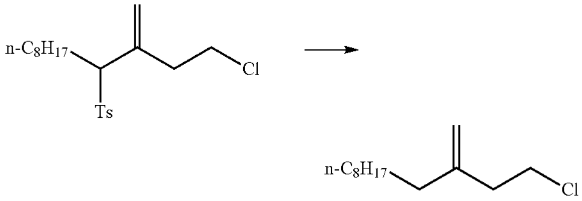

A solution of 1.7 M lithium triethylborohydride in tetrahydrofuran (15.7 ml) was added dropwise for 1 hour to a mixture of 1-chloro-3-methylenedodecan-4-yl p-tolyl sulfone (5.50 g) synthesized in the aforesaid Synthetic Example 6, 1,3-bis(diphenylphosphino)propane palladium (II) chloride (0.440 g), and tetrahydrofuran (150 ml) in a nitrogen atmosphere under ice cooling with stirring. The reaction mixture was stirred under ice cooling for 100 minutes, an aqueous solution (100 g) of 12.5% sodium hydroxide was added dropwise, and then 35% aqueous hydrogen peroxide (11.5 g) was added dropwise. The fractionated organic layer was subjected to ordinary work-ups, i.e., washing, drying, and concentration, and then purified by silica gel column chromatography. A 4.7:46.5:48.8 ($^1$H-NMR) mixture of target compound 2-(2-chloroethyl)-1-undecene: target compound (E)-1-chloro-3-methyl-3-dodecene:target compound isomer (Z)-1-chloro-3-methyl-3-dodecene (isomer total yield 94%) was obtained.

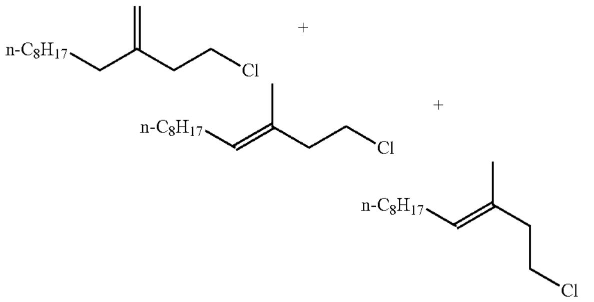

Similarly to the aforesaid Example, the stereospecificity and reaction selectivity of the desulfonation reaction of this Synthetic Example were poor, resulting in a mixture of these isomers due to allylic rearrangement, specifically, the double bond rearranging from the exo-position toward the trisubstituted side.

The substrate of the reaction had the same substituent groups as the secondary sulfone compound of the general formula (H), that is, an exo-methylene group at position 3 and an arylsulfonyl group at position 4, which suggests that it is inappropriate to synthesize the halogen compound of the general formula (D) by desulfonation of the secondary sulfone compound of the general formula (H).

Example 12: Synthesis of (E)-7-chloro-5-methylene-1-phenyl-1-heptene (when $R^1$=H, $R^2$=Ph, and Z=Cl in the general formula (D))

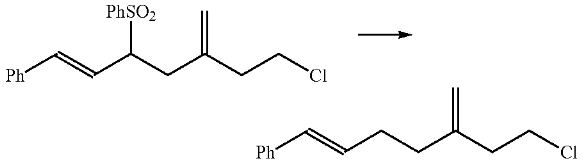

A solution of 1.0 M lithium triethylborohydride in tetrahydrofuran (18.0 ml) was added dropwise for 1 hour to a mixture of 7-chloro-5-methylene-1-phenyl-1-hepten-3-yl phenyl sulfone (5.00 g) synthesized in the aforesaid Example 3, 1,3-bis(diphenylphosphino)propane palladium (II) chloride (0.410 g), and tetrahydrofuran (100 ml) in a nitrogen atmosphere under ice cooling with stirring. The reaction mixture was stirred for 1 hour under ice cooling, an aqueous solution (64 g) of 12.5% sodium hydroxide was added dropwise, and then 35% aqueous hydrogen peroxide (7.0 g) was added dropwise. The fractionated organic layer was subjected to ordinary work-ups, i.e., washing, drying, and concentration, and then purified by silica gel column chromatography to obtain the target compound, (E)-7-chloro-5-methylene-1-phenyl-1-heptene (2.02 g, 97.0% GC, yield 66%).

(E)-7-Chloro-3-methylene-1-phenyl-1-heptene

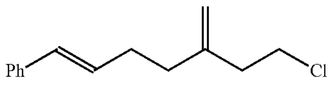

$C_{14}H_{17}Cl$

Colorless Oil

IR (D-ATR): ν=3081, 3060, 3025, 2998, 2932, 2847, 1947, 1873, 1800, 1647, 1598, 1577, 1493, 1447, 1326, 1299, 1069, 1029, 964, 897, 743, 693, 658 $cm^{-1}$.

$^1$H-NMR (500 MHz, $CDCl_3$): δ=2.22 (2H, t-like, J=~8 Hz), 2.35-2.42 (2H, m), 2.54 (2H, dt, J=0.6, 7.3 Hz), 3.64 (2H, t, J=7.3 Hz), 4.88 (1H, s-like), 4.94 (1H, s-like), 6.22 (1H, dt, J=15.9, 6.8 Hz), 6.42 (1H, d, J=~16 Hz), 7.18-7.23 (1H, m), 7.28-7.38 (4H, m) ppm.

$^{13}$C-NMR (125 MHz, $CDCl_3$): δ=31.10, 35.48, 39.10, 42.71, 112.10, 125.94, 126.94, 128.48, 129.77, 130.30, 137.60, 144.89 ppm.

GC-MS (EI, 70 eV): 39, 51, 65, 77, 91, 104, 117 (base peak), 129, 141, 157, 179, 191, 205, 220 ($M^+$).

Examples: Synthesis of Secondary Allylsulfone Compound of the Following General Formula (E)

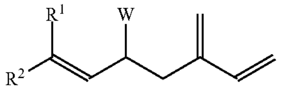

(E)

Example 13: Synthesis of (E)-7,11-dimethyl-3-methylene-1,6,10-dodecatrien-5-yl p-tolyl sulfone (when $R^1$=$CH_3$, $R^2$=4-methyl-3-pentenyl group, and W=p-toluenesulfonyl group in the general formula (E))

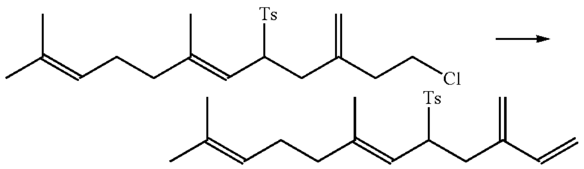

A mixture of (E)-1-chloro-7,11-dimethyl-3-methylene-6,10-dodecadien-5-yl p-tolyl sulfone (3.26 g, ~100% NMR) synthesized by a process similar to that of the aforesaid Example 1, 2,6-di-t-butyl-p-cresol (BHT; 0.05 g), and 1,8-diazabicyclo[5.4.0]-7-undecene (DBU; 6.30 g) was stirred for 2 hours at 80° C. in a nitrogen atmosphere. The reaction mixture was cooled and then extracted with ethyl acetate. The ethyl acetate solution was subjected to ordinary work-ups, i.e., washing, drying, and concentration to obtain the target compound, (E)-7,11-dimethyl-3-methylene-1,6,10-dodecatrien-5-yl p-tolyl sulfone (3.19 g, quantitative yield).

(E)-7,11-Dimethyl-3-methylene-1,6,10-dodecatrien-5-yl p-tolyl sulfone

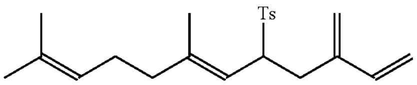 [SMILES: C=CC(=C)CC(/C=C(\C)CCC=C(C)C)S(=O)(=O)c1ccc(C)cc1]

$C_{22}H_{30}O_2S$

Yellowish Oil

IR (D-ATR): ν=2967, 2924, 2856, 1596, 1446, 1382, 1313, 1301, 1288, 1144, 1086, 905, 815, 752, 670, 579 $cm^{-1}$.

$^1$H-NMR (500 MHz, $CDCl_3$): δ=1.16 (3H, d, J=1.3 Hz), 1.58 (3H, d, J=0.6 Hz), 1.67 (3H, s), 1.89-1.99 (4H, m), 2.36 (1H, dd, J=11.3, 13.8 Hz), 2.43 (3H, s), 3.23 (1H, d-like, J=~13 Hz), 3.96 (1H, dt-like, J=~2, 11 Hz), 4.89-4.92 (1H, m), 4.92 (1H, s), 4.97-5.03 (1H, m), 5.02 (1H, s), 5.08 (1H, d-like, J=~11 Hz), 5.26 (1H, d-like, J=17 Hz), 6.29 (1H, dd, J=11.0, 17.8 Hz), 7.30 (2H, d-like, J=~8 Hz), 7.73 (2H, d-like, J=~8 Hz) ppm.

$^{13}$C-NMR (125 MHz, $CDCl_3$): δ=16.38, 17.63, 21.62, 25.64, 26.14, 30.38, 39.64, 63.25, 114.15, 117.20, 118.78, 123.62, 129.21, 129.35, 131.79, 134.98, 137.72, 141.25, 144.34, 145.55 ppm.

Example 14: Synthesis of (Z)-7,11-dimethyl-3-methylene-1,6,10-dodecatrien-5-yl p-tolyl sulfone (when $R^1$=4-methyl-3-pentenyl group, $R^2$=$CH_3$, and W=p-Toluenesulfonyl Group in the General Formula (E))

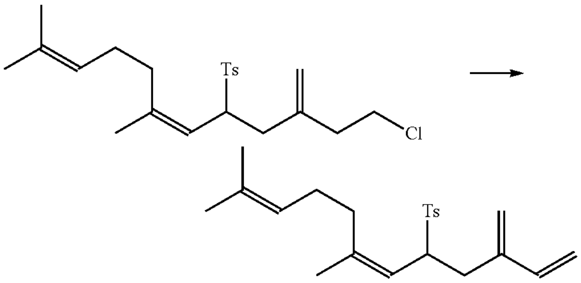

A mixture of potassium tert-butoxide (7.50 g) and tetrahydrofuran (70 ml) was added dropwise for 45 minutes to a mixture of (Z)-1-chloro-7,11-dimethyl-3-methylene-6,10-dodecadien-5-yl p-tolyl sulfone (20.0 g, 85.8% NMR, including (Z)-1-(2,6-dimethyl-1,5-heptadienyl)-3-methylenecyclopentan-1-yl p-tolyl sulfone (14.1% NMR) as an impurity) synthesized in the aforesaid Example 2 and tetrahydrofuran (50 ml) in a nitrogen atmosphere under ice cooling with stirring. The reaction mixture was stirred for 40 minutes while cooled, poured into an aqueous solution of ammonium chloride, and then extracted with ethyl acetate. The ethyl acetate solution was subjected to ordinary work-ups, i.e., washing, drying, and concentration, and then purified by silica gel column chromatography to obtain a 73:27 ($^1$H-NMR) mixture of target compound (Z)-7,11-dimethyl-3-methylene-1,6,10-dodecatrien-5-yl p-tolyl sulfone: target compound isomer (Z)-1-(2,6-dimethyl-1,5-heptadienyl)-3-methylenecyclopentan-1-yl p-tolyl sulfone from starting material (15.48 g, ~73% NMR, purity calculated yield 85%).

A part of the mixture was purified by silica gel column chromatography and subjected to spectra measurement.

(Z)-7,11-Dimethyl-3-methylene-1,6,10-dodecatrien-5-yl p-tolyl sulfone

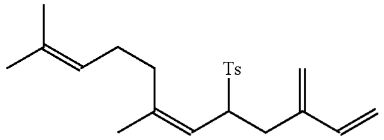 [SMILES: C=CC(=C)CC(/C=C(/C)CCC=C(C)C)S(=O)(=O)c1ccc(C)cc1]

$C_{22}H_{30}O_2S$

Yellowish Oil

IR (D-ATR): ν=2968, 2917, 2858, 1597, 1447, 1377, 1313, 1300, 1288, 1144, 1086, 906, 815, 752, 680, 578 $cm^{-1}$.

$^1$H-NMR (500 MHz, $CDCl_3$): δ=1.40-1.75 (4H, m), 1.51 (3H, s), 1.63 (3H, br.s), 1.65 (3H, d-like, J=~1 Hz), 2.33 (1H, dd, J=11.1, 13.6 Hz), 2.43 (3H, s), 3.20 (1H, d-like m, J=~13 Hz), 3.95 (1H, dt-like, J=~2, 11 Hz), 4.85-4.95 (2H, m), 4.93 (1H, s), 5.03 (1H, s-like), 5.08 (1H, d-like, J=~11 Hz), 5.23 (1H, d-like, J=18 Hz), 6.27 (1H, dd, J=10.9, 17.7 Hz), 7.29-7.33 (2H, m), 7.69-7.75 (2H, m) ppm.

$^{13}$C-NMR (125 MHz, $CDCl_3$): δ=17.61, 21.61, 23.31, 25.57, 26.10, 30.67, 32.07, 63.05, 114.25, 117.40, 119.18, 123.63, 129.20, 129.36, 130.21, 131.78, 137.62, 141.12, 144.36, 145.80 ppm.

GC-MS (EI, 70 eV, deformed peak): 41, 69 (base peak), 81, 91, 109, 113, 161, 187, 205.

Examples: Synthesis of Secondary Allylsulfonediene Compound of the Following General Formula (F)

(F)

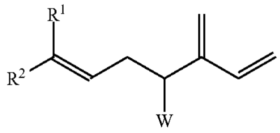

Example 15: Synthesis of (Z)-7,11-dimethyl-3-methylene-1,6,10-dodecatrien-4-yl p-tolyl sulfone (when $R^1$=4-methyl-3-pentenyl group, $R^2$=$CH_3$, and W=p-Toluenesulfonyl Group in the General Formula (F))

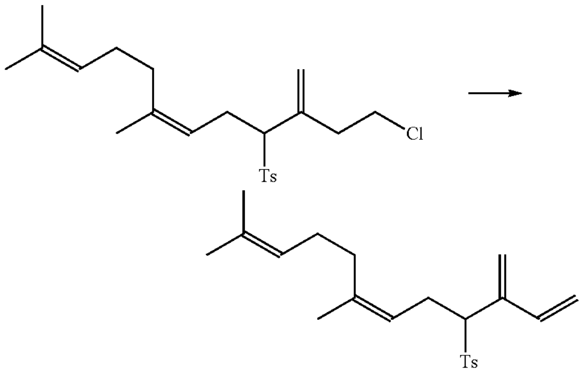

A mixture of (Z)-1-chloro-7,11-dimethyl-3-methylene-6,10-dodecadien-4-yl p-tolyl sulfone (5.00 g, ~96% NMR) synthesized by a process similar to that of the aforesaid Example 5, 2,6-di-t-butyl-p-cresol (BHT; 0.03 g), and 1,8-diazabicyclo[5.4.0]-7-undecene (DBU; 9.28 g) was stirred for 3 hours at 40 to 60° C. in a nitrogen atmosphere. The reaction mixture was cooled, poured into dilute hydrochloric acid, and then extracted with ethyl acetate. The ethyl acetate solution was subjected to ordinary work-ups, i.e., washing, drying, and concentration, and then purified by silica gel column chromatography to obtain the target compound, (Z)-7,11-dimethyl-3-methylene-1,6,10-dodecatrien-4-yl p-tolyl sulfone (3.09 g, yield 71%).

(Z)-7,11-Dimethyl-3-methylene-1,6,10-dodecatrien-4-yl p-tolyl sulfone

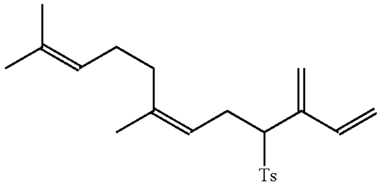 [SMILES: C=CC(=C)C(C/C=C(/C)CCC=C(C)C)S(=O)(=O)c1ccc(C)cc1]

$C_{22}H_{30}O_2S$

Yellowish Oil

IR (D-ATR): ν=3090, 2965, 2918, 2858, 1632, 1596, 1494, 1445, 1402, 1377, 1316, 1301, 1289, 1146, 1086, 1039, 1019, 986, 907, 815, 707, 670 $cm^{-1}$.

$^1$H-NMR (500 MHz, $CDCl_3$): δ=1.60 (3H, d, J=0.8 Hz), 1.62 (3H, d, J=1.3 Hz), 1.69 (3H, br.s), 1.90-2.02 (4H, m), 2.42 (3H, s), 2.49-2.60 (1H, m), 2.88-2.98 (1H, m), 3.83 (1H, dd, J=11.4, 3.7 Hz), 4.89 (1H, dt-like, J=1.3, ~7 Hz), 4.96 (1H, d, J=10.9 Hz), 5.01-5.08 (1H, m), 5.14 (1H, d, J=17.5 Hz), 5.26 (1H, s), 5.41 (1H, d-like, J=0.4 Hz), 6.28 (1H, ddd, J=17.6, 10.9, 0.7 Hz), 7.23-7.32 (2H, m), 7.64-7.73 (2H, m) ppm.

$^{13}$C-NMR (125 MHz, $CDCl_3$): δ=17.61, 21.58, 23.30, 25.71, 26.32, 26.62, 31.96, 65.87, 114.34, 119.02, 121.85, 123.85, 129.30, 129.32, 131.80, 134.85, 137.22, 138.57, 138.72, 144.38 ppm.

GC-MS (EI, 70 eV, deformed peak): 41, 69 (base peak), 81, 91, 108, 133, 159, 183, 203, 358 ($M^+$).

Example 16: Synthesis of 7-methyl-3-methylen-1,6-octadienen-4-yl p-tolyl sulfone (when $R^1$=$R^2$=$CH_3$ and W=p-Toluenesulfonyl Group in the General Formula (F))

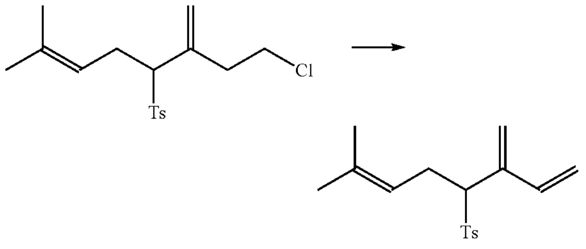

A mixture of 1-chloro-7-methyl-3-methylen-6-octen-4-yl p-tolyl sulfone (1.00 g, 97.4% GC) synthesized in the aforesaid Example 6, potassium tert-butoxide (0.75 g), and tetrahydrofuran (THF; 25 ml) was stirred in a nitrogen atmosphere for 30 minutes under ice cooling, and then for 18 hours at a room temperature. The reaction mixture was cooled, poured into saturated brine, and then extracted with ethyl acetate. The ethyl acetate solution was subjected to ordinary work-ups, i.e., washing, drying, and concentration, and then purified by silica gel column chromatography to obtain the target compound, 7-methyl-3-methylen-1,6-octadienen-4-yl p-tolyl sulfone (0.48 g, yield 55%).

7-Methyl-3-methylen-1,6-octadienen-4-yl p-tolyl sulfone

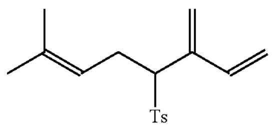 [SMILES: C=CC(=C)C(CC=C(C)C)S(=O)(=O)c1ccc(C)cc1]

$C_{17}H_{22}O_2S$ $^1$H-NMR (500 MHz, $CDCl_3$): δ=1.57 (3H, s), 1.62 (3H, d-like, J=~1.1 Hz), 2.42 (3H, s), 2.51-2.60 (1H, m), 2.88-2.95 (1H, m), 3.86 (1H, dd, J=3.8, 11.3 Hz), 4.86-4.91 (1H, m), 4.95 (1H, d, J=10.9 Hz), 5.12 (1H, d, J=17.6 Hz), 5.26 (1H, s), 5.39 (1H, s), 6.24 (1H, ddd-like, J=0.5, 10.9, 17.5 Hz), 7.25-7.32 (2H, m), 7.68-7.75 (2H, m) ppm.

GC-MS (EI, 70 eV, deformed peak): 41, 55, 69, 77, 91 (base peak), 105, 119, 134, 157, 290 ($M^+$).

Examples: Synthesis of 2-(3-Alkenyl)-1,3-Butadiene Compound of the Following General Formula (A)

(A)

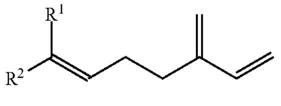

Example 17: Synthesis (1) of (E)-β-farnesene (when $R^1$=$CH_3$ and $R^2$=4-methyl-3-Pentenyl Group in the General Formula (A))

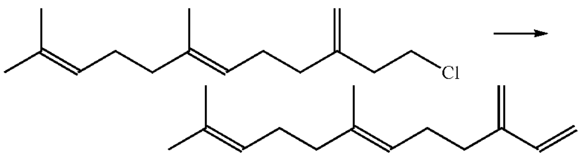

A mixture of potassium tert-butoxide (5.32 g) and tetrahydrofuran (50 ml) was added dropwise for 25 minutes to a mixture of (E)-12-chloro-2,6-dimethyl-10-methylene-2,6-dodecadiene (9.31 g, 98.9% GC) synthesized by a process similar to that of the aforesaid Example 9, 2,6-di-t-butyl-p-cresol (BHT; 0.03 g), and tetrahydrofuran (100 ml) in a nitrogen atmosphere under ice cooling with stirring. The reaction mixture was stirred for 2.5 hours under ice cooling, poured into an aqueous solution of ammonium chloride, and then extracted with diethyl ether. The diethyl ether solution was subjected to ordinary work-ups, i.e., washing, drying, and concentration, and then distilled at a reduced pressure to obtain the target compound, (E)-β-farnesene (7.87 g, 94.4 to 96.5% GC, quantitative yield).

(E)-β-Farnesene

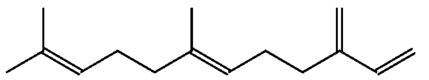

$C_{15}H_{24}$

Colorless Oil

Boiling point: 73 to 74° C./0.1 kPa

IR (D-ATR): v=3089, 2967, 2926, 2856, 1595, 1442, 1377, 990, 893 $cm^{-1}$.

$^1$H-NMR (500 MHz, $CDCl_3$): δ=1.61 (6H, br.s), 1.69 (3H, br.s.), 1.96-2.02 (2H, m), 2.04-2.11 (2H, m), 2.17-2.27 (4H, m), 5.00 (1H, br.s), 5.02 (1H, br.s), 5.06 (1H, d-like, J=~11 Hz), 5.08-5.13 (1H, m), 5.15-5.19 (1H, m), 5.25 (1H, d-like, J=~18 Hz), 6.38 (1H, dd, J=~11, 18 Hz) ppm.

$^{13}$C-NMR (125 MHz, $CDCl_3$): δ=16.01, 17.67, 25.68, 26.60, 26.70, 31.40, 39.69, 113.03, 115.70, 124.01, 124.35, 131.29, 135.37, 138.99, 146.12 ppm.

GC-MS (EI, 70 eV): 27, 41, 55, 69 (base peak), 81, 93, 107, 120, 133, 148, 161, 175, 189, 204 ($M^+$).

Example 18: Synthesis (2) of (E)-β-farnesene (when $R^1$=$CH_3$ and $R^2$=4-methyl-3-Pentenyl Group in the General Formula (A))

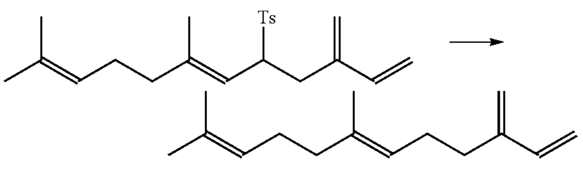

A solution of 1.7 M lithium triethylborohydride in tetrahydrofuran (12.0 ml) was added dropwise for 1 hour to a mixture of (E)-7,11-dimethyl-3-methylene-1,6,10-dodecatrien-5-yl p-tolyl sulfone (2.44 g, 78.1% NMR, including (E)-1-(2,6-dimethyl-1,5-heptadienyl)-3-methylenecyclopentan-1-yl p-tolyl sulfone (21.9% NMR) as an impurity) synthesized by a process similar to the aforesaid Example 13, 1,3-bis(diphenylphosphino)propane palladium(II) chloride (0.80 g), and tetrahydrofuran (25 ml) in a nitrogen atmosphere under ice cooling with stirring. The reaction temperature was gradually raised to a room temperature and stirred for 1 hour. The reaction mixture was ice-cooled, an aqueous solution (25 g) of 12.5% sodium hydroxide was added dropwise, and then 35% aqueous hydrogen peroxide (3.75 g) was added dropwise. The reaction mixture was extracted with n-hexane. The n-hexane solution was subjected to ordinary work-ups, i.e., washing, drying, and concentration, and then purified by silica gel column chromatography to obtain a 73:27 ($^1$H-NMR) mixture of target compound (E)-β-farnesene: target compound cyclic isomer (E)-1-(2,6-dimethyl-1,5-heptadienyl)-3-methylenecyclopentane (1.04 g, 57.5 to 67.2% GC, isomer total 83.4 to 92.5% GC, purity calculated yield 44%, purity reduced isomer total yield 63%).

(E)-1-(2,6-Dimethyl-1,5-heptadienyl)-3-methylene-cyclopentane

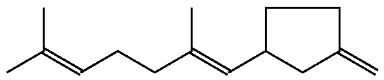

$C_{15}H_{24}$

Colorless Oil $^{13}$C-NMR (150 MHz, $CDC_3$): δ=16.47, 17.83, 25.84, 26.84, 32.52, 33.88, 39.20, 39.78, 40.78, 104.96, 124.46, 129.07, 131.48, 134.74, 153.01 ppm.

GC-MS (EI, 70 eV): 27, 41, 55, 69 (base peak), 81, 93, 107, 123, 135, 148, 161, 176, 189, 204 ($M^+$).

Example 19: Synthesis (3) of (E)-β-farnesene (when $R^1$=$CH_3$ and $R^2$=4-methyl-3-Pentenyl Group in the General Formula (A))

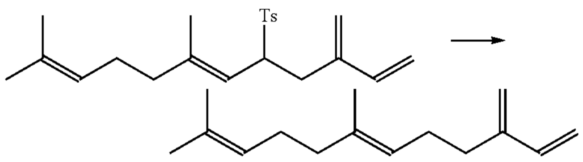

All of metallic magnesium (1.70 g) was added simultaneously to a mixture of (E)-7,11-dimethyl-3-methylene-1,6,10-dodecatrien-5-yl p-tolyl sulfone (2.50 g, ~100% NMR) synthesized in the aforesaid Example 13, 2,6-di-t-butyl-p-cresol (BHT; 0.05 g), and methanol (40 ml) in a nitrogen atmosphere with stirring at a room temperature. Hydrogen was produced with heat generation up to 37° C. at the start of the reaction. The heat generation due to the initial heat of reaction was held at 30 to 37° C. in an ice bath, and then the reaction mixture was stirred for 3 hours at a room temperature. The reaction mixture was ice-cooled. 10% Hydrochloric acid was added to the reaction mixture, and then the reaction mixture was extracted with diethyl ether. The diethyl ether solution was subjected to ordinary work-ups, i.e., washing, drying, and concentration to obtain a 66.5:33.5 (GC) mixture of target compound (E)-β-farnesene: target compound isomer (E)-7,11-dimethyl-3-methylene-1,5,9-dodecatriene having trisubstituted double bond at position 6 rearranged to (E)-disubstituted double bond at position 5 (1.34 g, isomer total quantitative yield).

(E)-7,11-Dimethyl-3-methylene-1,5,9-dodecatriene

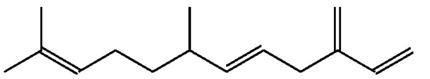

$C_{15}H_{24}$

Colorless Oil $^{13}$C-NMR (150 MHz, $CDCl_3$): δ=17.82, 20.93, 25.87, 26.04, 34.79, 36.55, 37.35, 113.70, 116.42, 124.92, 125.73, 131.32, 138.48, 138.91, 145.65 ppm.

GC-MS (EI, 70 eV): 27, 41, 55, 67, 69, 79 (base peak), 81, 93, 105, 119, 133, 147, 161, 175, 189, 204 ($M^+$).

Example 20: Synthesis (1) of (Z)-β-farnesene (when $R^1$=4-methyl-3-pentenyl group and $R^2$=$CH_3$ in the General Formula (A))

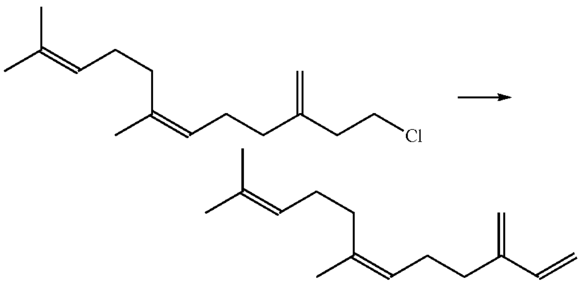

A mixture of (Z)-12-chloro-2,6-dimethyl-10-methylene-2,6-dodecadiene (1.81 g, 97% GC) synthesized in the aforesaid Example 10, 2,6-di-t-butyl-p-cresol (BHT; 0.03 g), and 1,8-diazabicyclo[5.4.0]-7-undecene (DBU; 4.60 g) was stirred for 4.5 hours at 80° C. in a nitrogen atmosphere. The reaction mixture was cooled, poured into dilute hydrochloric acid, and then extracted with diethyl ether. The diethyl ether solution was subjected to ordinary work-ups, i.e., washing, drying, and concentration, and then distilled at a reduced pressure to obtain the target compound, (Z)-β-farnesene (1.37 g, 97.9 to 98.1% GC, 94.3 to 95.8% Z, yield 92%).

(Z)-β-Farnesene

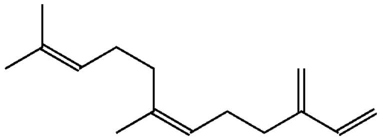

$C_{15}H_{24}$

Colorless Oil

IR (D-ATR): ν=3089, 2966, 2928, 2857, 1595, 1448, 1376, 990, 893 $cm^{-1}$.

$^{1}$H-NMR (500 MHz, $CDCl_3$): δ=1.61 (3H, br.s), 1.69 (3H, br.s.), 1.70 (3H, t, J=~1 Hz), 1.99-2.10 (4H, m), 2.15-2.25 (4H, m), 5.00 (1H, s-like), 5.01 (1H, s-like), 5.06 (1H, dq-like, J=~11, ~1 Hz), 5.09-5.14 (1H, m), 5.15-5.19 (1H, m), 5.25 (1H, dt-like, J=~18, ~0.6 Hz), 6.38 (1H, dd, J=~11, 18 Hz) ppm.

$^{13}$C-NMR (125 MHz, $CDCl_3$): δ=17.62, 23.36, 25.70, 26.51, 26.60, 31.66, 31.97, 113.08, 115.66, 124.29, 124.82, 131.57, 135.53, 138.95, 146.15 ppm.

GC-MS (EI, 70 eV): 27, 41, 55, 69 (base peak), 81, 93, 107, 120, 133, 148, 161, 175, 189, 204 ($M^+$).

Example 21: Synthesis (2) of (Z)-β-farnesene (when $R^1$=4-methyl-3-pentenyl group and $R^2$=$CH_3$ in the general formula (A))

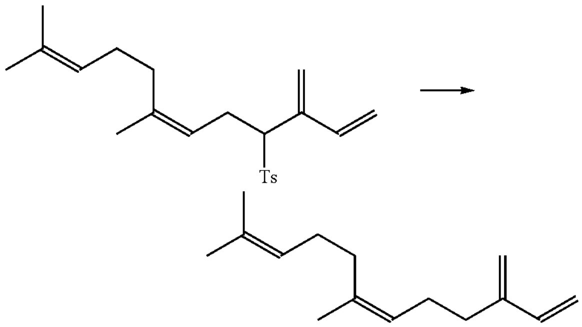

A solution of 1.7 M lithium triethylborohydride in tetrahydrofuran (3.5 ml) was poured for 5 minutes into a mixture of (Z)-7,11-dimethyl-3-methylene-1,6,10-dodecatrien-4-yl p-tolyl sulfone (4.88 g, 95% NMR) synthesized in the aforesaid Example 15, 2,6-di-t-butyl-p-cresol (BHT; 0.03 g), 1,3-bis(diphenylphosphino)propane palladium(II) chloride (0.29 g), and tetrahydrofuran (80 ml) in a nitrogen atmosphere under ice cooling with stirring. The reaction mixture was stirred for 45 minutes under ice cooling, an aqueous solution (7.5 g) of 12.5% sodium hydroxide was added dropwise, and then 35% aqueous hydrogen peroxide (1.20 g) was added dropwise. Water (20 ml) was added to the reaction mixture, and an organic layer was fractionated. The organic layer was subjected to ordinary work-ups, i.e., washing, drying, and concentration to obtain a crude product (1.36 g) of a complex isomeric mixture of the target compound, (Z)-β-farnesene, target compound isomers, (E)-β-farnesene, (Z, Z)-3,7,11-trimethyl-1,3,6,10-dodecatetraene, and (Z)-α-farnesene, and other isomers.

Example 22: Synthesis (3) of (Z)-β-farnesene (when $R^1$=4-methyl-3-pentenyl group and $R^2$=$CH_3$ in the General Formula (A))

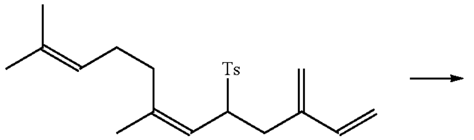

-continued

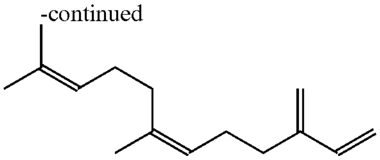

A solution of 1.7 M lithium triethylborohydride in tetrahydrofuran (19.3 ml) was added dropwise for 30 minutes to a mixture of (Z)-7,11-dimethyl-3-methylene-1,6,10-dodecatrien-5-yl p-tolyl sulfone (5.89 g, ≥~59% GC (approximate value due to decomposition in GC), including (Z)-1-(2,6-dimethyl-1,5-heptadienyl)-3-methylenecyclopentan-1-yl p-tolyl sulfone as an impurity (≥~40% GC (approximate value due to decomposition in GC))) synthesized in the aforesaid Example 14, 1,3-bis(diphenylphosphino)propane palladium(II) chloride (2.00 g), and tetrahydrofuran (60 ml) in a nitrogen atmosphere under ice cooling with stirring. The reaction temperature was gradually raised to a room temperature and stirred for 16 hours. The reaction mixture was ice-cooled, an aqueous solution (40.2 g) of 12.5% sodium hydroxide was added dropwise, and then 35% aqueous hydrogen peroxide (6.05 g) was added dropwise. Water was added to the reaction mixture, and the reaction mixture was extracted with diethyl ether. The diethyl ether solution was subjected to ordinary work-ups, i.e., washing, drying, and concentration to obtain a crude product (3.92 g) of a 59:42 (GC) mixture of target compound (Z)-β-farnesene: target compound cyclic isomer (Z)-1-(2,6-dimethyl-1,5-heptadienyl)-3-methylenecyclopentane and a mixture of isomers including multiple minor isomers.

(Z)-1-(2,6-Dimethyl-1,5-heptadienyl)-3-methylenecyclopentane

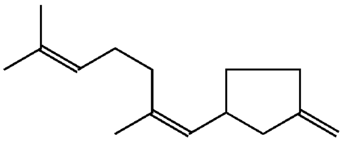

Example 23: Synthesis (4) of (Z)-β-farnesene (when $R^1$=4-methyl-3-pentenyl group and $R^2$=$CH_3$ in the General Formula (A))

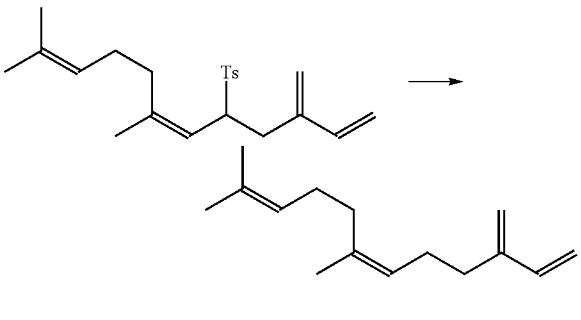

A solution of 1.0 M lithium triethylborohydride in tetrahydrofuran (55.2 ml) was added dropwise for 30 minutes to a mixture of (Z)-7,11-dimethyl-3-methylene-1,6,10-dodecatrien-5-yl p-tolyl sulfone (9.00 g, ≥~51% GC (approximate value due to decomposition in GC), including (Z)-1-(2,6-dimethyl-1,5-heptadienyl)-3-methylenecyclopentan-1-yl p-tolyl sulfone as an impurity) synthesized in the aforesaid Example 14, 1,3-bis(diphenylphosphino)propane palladium (II) chloride (1.48 g), and tetrahydrofuran (80 ml) in a nitrogen atmosphere under ice cooling with stirring. The reaction temperature was gradually raised to a room temperature and stirred for 17 hours. The reaction mixture was ice-cooled, an aqueous solution (68.5 g) of 12.5% sodium hydroxide was added dropwise, and then 35% aqueous hydrogen peroxide (10.3 g) was added dropwise. Water was added to the reaction mixture, and the reaction mixture was extracted with diethyl ether. The diethyl ether solution was subjected to ordinary work-ups, i.e., washing, drying, and concentration to obtain a crude product (5.10 g) of a 59:42 complex isomer mixture of target compound (Z)-β-farnesene: target compound cyclic isomer (Z)-1-(2,6-dimethyl-1,5-heptadienyl)-3-methylenecyclopentane, and including multiple minor isomers.

Example 24: Synthesis of (E)-3-methylene-7-phenyl-1,6-heptadiene (when $R^1$=H and $R^2$=Ph=phenyl group in the general formula (A))

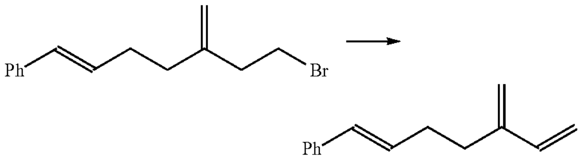

1,8-Diazabicyclo[5.4.0]-7-undecene (DBU; 610 μl) was added to a mixture of (E)-7-chloro-5-methylene-1-phenyl-1-heptene (500 mg, 97% GC) synthesized in the aforesaid Example 12, sodium bromide (50 mg), and N-methyl-2-pyrrolidone (8 ml) in a nitrogen atmosphere. The reaction mixture was stirred for 20 hours under heated conditions at 70 to 80° C. The reaction mixture was cooled, n-hexane was added, and the n-hexane solution was subjected to ordinary work-ups, i.e., washing, drying, and concentration, and then purified by silica gel column chromatography to obtain the target compound, (E)-3-methylene-7-phenyl-1,6-heptadiene (390 mg, 98.5% GC, 100% E, yield 94%).

(E)-3-Methylene-7-phenyl-1,6-heptadiene

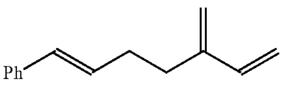

$C_{14}H_{16}$

Colorless Oil

IR (D-ATR): ν=3083, 3060, 3025, 2929, 2853, 1595, 1496, 1446, 1391, 1307, 1230, 1156, 1069, 991, 963, 896, 742, 692 $cm^{-1}$.

$^1$H-NMR (500 MHz, $CDCl_3$): δ=2.38-2.48 (4H, m), 5.07 (2H, d-like, J=7.2 Hz), 5.11 (1H, d-like, J=11 Hz), 5.29 (1H, d-like, J=18 Hz), 6.27 (1H, dt, J=15.8, 6.5 Hz), 6.42 (1H, dd, J=11, 18 Hz), 6.43 (1H, d-like, J=15.8 Hz), 7.19-7, 23 (1H, m), 7.29-7.33 (2H, m), 7.35-7.38 (2H, m) ppm.

$^{13}$C-NMR (125 MHz, $CDCl_3$): δ=31.09, 31.56, 113.27, 116.07, 125.94, 126.88, 128.46, 130.06, 130.28, 137.72, 138.81, 145.56 ppm.

GC-MS (EI, 70 eV): 27, 39, 51, 65, 77, 93, 104, 117 (base peak), 128, 141, 155, 169, 184 ($M^+$).

The invention claimed is:

1. A process for preparing a 2-(3-alkenyl)-1,3-butadiene compound of the following general formula (A):

(A)

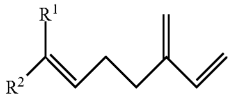

wherein $R^1$ and $R^2$ represent, independently of each other, a hydrogen atom or a linear, branched, or cyclic hydrocarbon group having 1 to 20 carbon atoms and optionally having an unsaturated bond(s), the process comprising the step of:

subjecting a secondary allylsulfone compound of the following general formula (G):

(G)

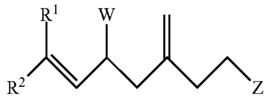

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to a reductive removal of an arenesulfonyl group, W, at an allyl position, and then subjecting the secondary allylsulfone compound (G) to an elimination reaction of a hydrogen halide, HZ, in this order or in reverse order, to form the 2-(3-alkenyl)-1,3-butadiene compound (A).

2. The process according to claim 1, wherein one of $R^1$ and $R^2$ represents a methyl group and the other of $R^1$ and $R^2$ represents a 4-methyl-3-pentenyl group or a methyl group.

3. A process for preparing a 2-(3-alkenyl)-1,3-butadiene compound of the following general formula (A):

(A)

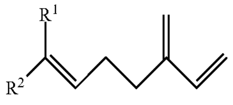

wherein $R^1$ and $R^2$ represent, independently of each other, a hydrogen atom or a linear, branched, or cyclic hydrocarbon group having 1 to 20 carbon atoms and optionally having an unsaturated bond(s), the process comprising the steps of:

subjecting a secondary allylsulfone compound of the following general formula (G):

(G)

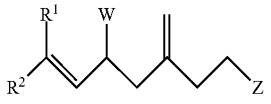

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to a reductive removal of an arenesulfonyl group, W, at an allyl position to form a halide compound of the following general formula (D):

(D)

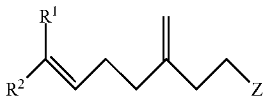

wherein $R^1$ and $R^2$ represent, independently of each other, a hydrogen atom or a linear, branched, or cyclic hydrocarbon group having 1 to 20 carbon atoms and optionally having an unsaturated bond(s), and Z represents a halogen atom; and subjecting the halide compound (D) thus obtained to an elimination reaction of a hydrogen halide, HZ, to form the 2-(3-alkenyl)-1,3-butadiene compound (A).

4. The process according to claim 3, wherein one of $R^1$ and $R^2$ represents a methyl group and the other of $R^1$ and $R^2$ represents a 4-methyl-3-pentenyl group or a methyl group.

5. A process for preparing a 2-(3-alkenyl)-1,3-butadiene compound of the following general formula (A):

(A)

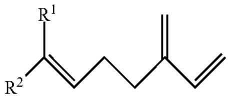

wherein $R^1$ and $R^2$ represent, independently of each other, a hydrogen atom or a linear, branched, or cyclic hydrocarbon group having 1 to 20 carbon atoms and optionally having an unsaturated bond(s), the process comprising the steps of:

subjecting a secondary allylsulfone compound of the following general formula (G):

(G)

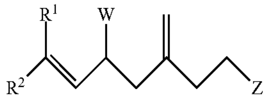

wherein $R^1$ and $R^2$ represent, independently of each other, a hydrogen atom or a linear, branched, or cyclic hydrocarbon group having 1 to 20 carbon atoms and optionally having an unsaturated bond(s), W represents an arenesulfonyl group, and Z represents a halogen atom, to an elimination reaction of a hydrogen halide, HZ, to form a secondary allylsulfone compound of the following general formula (E):

(E)

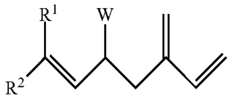

wherein $R^1$ and $R^2$ represent, independently of each other, a hydrogen atom or a linear, branched, or cyclic hydrocarbon group having 1 to 20 carbon atoms and optionally having an unsaturated bond(s), and W represents an arenesulfonyl group; and subjecting the secondary allylsulfone compound (E) thus obtained to a reductive removal of an arenesulfonyl group, W, at an allyl position to form the 2-(3-alkenyl)-1,3-butadiene compound (A).

6. The process according to claim 5, wherein one of $R^1$ and $R^2$ represents a methyl group and the other of $R^1$ and $R^2$ represents a 4-methyl-3-pentenyl group or a methyl group.

* * * * *